(12) United States Patent
Warren

(10) Patent No.: US 6,478,850 B2
(45) Date of Patent: Nov. 12, 2002

(54) MINIATURIZED WEARABLE OXYGEN CONCENTRATOR

(75) Inventor: John Lee Warren, Salmon Arm (CA)

(73) Assignee: Wearair Oxygen Inc., Kelowna (CA)

(*) Notice: Subject to any disclaimer, the term of this patent is extended or adjusted under 35 U.S.C. 154(b) by 0 days.

(21) Appl. No.: 10/092,574

(22) Filed: Mar. 8, 2002

(65) Prior Publication Data

US 2002/0121191 A1 Sep. 5, 2002

Related U.S. Application Data

(63) Continuation-in-part of application No. 09/921,863, filed on Aug. 2, 2001.
(60) Provisional application No. 60/222,591, filed on Aug. 2, 2000.

(51) Int. Cl.[7] .............................................. B01D 53/047
(52) U.S. Cl. ................. 95/21; 95/98; 95/130; 96/115
(58) Field of Search ................. 95/11, 19, 21, 95/96, 98, 103, 130; 96/109, 110, 113, 114, 115, 121

(56) References Cited

U.S. PATENT DOCUMENTS

| 2,944,627 | A | | 7/1960 | Skarstrom | |
| 3,400,713 | A | | 9/1968 | Finan | |
| 4,222,750 | A | * | 9/1980 | Gauthier et al. | 95/102 |
| 4,516,424 | A | * | 5/1985 | Rowland | 73/1.06 |
| 4,685,939 | A | | 8/1987 | Kratz et al. | |
| 4,802,899 | A | * | 2/1989 | Vrana et al. | 96/109 |
| 5,104,426 | A | * | 4/1992 | Yamada et al. | 95/102 |
| 5,122,164 | A | * | 6/1992 | Hirooka et al. | 95/130 |
| 5,340,381 | A | * | 8/1994 | Vorih | 95/105 |
| 5,529,607 | A | * | 6/1996 | Tan | 95/100 |
| 5,531,807 | A | | 7/1996 | McCombs | |
| 5,540,758 | A | * | 7/1996 | Agrawal et al. | 95/101 |
| 5,850,833 | A | | 12/1998 | Kotliar | |
| 5,871,564 | A | | 2/1999 | McCombs | |
| 5,912,426 | A | * | 6/1999 | Smolarek et al. | 96/115 |
| 5,968,233 | A | * | 10/1999 | Rouge et al. | 95/101 |
| 6,003,744 | A | | 12/1999 | Culjak | |
| 6,238,458 | B1 | * | 5/2001 | Monereau | 95/101 |

* cited by examiner

Primary Examiner—David A. Simmons
Assistant Examiner—Frank M. Lawrence
(74) Attorney, Agent, or Firm—Antony C. Edwards

(57) ABSTRACT

A component gas concentrator includes an air compressor/vacuum pump, an air-tight first container containing a molecular sieve bed, the first container in fluid communication with the compressor/vacuum pump through a first gas conduit, and an air-tight second container in fluid communication with the first container through a second gas conduit. A gas flow controller such as PLC controls actuation of valves mounted to the gas conduits.

19 Claims, 16 Drawing Sheets

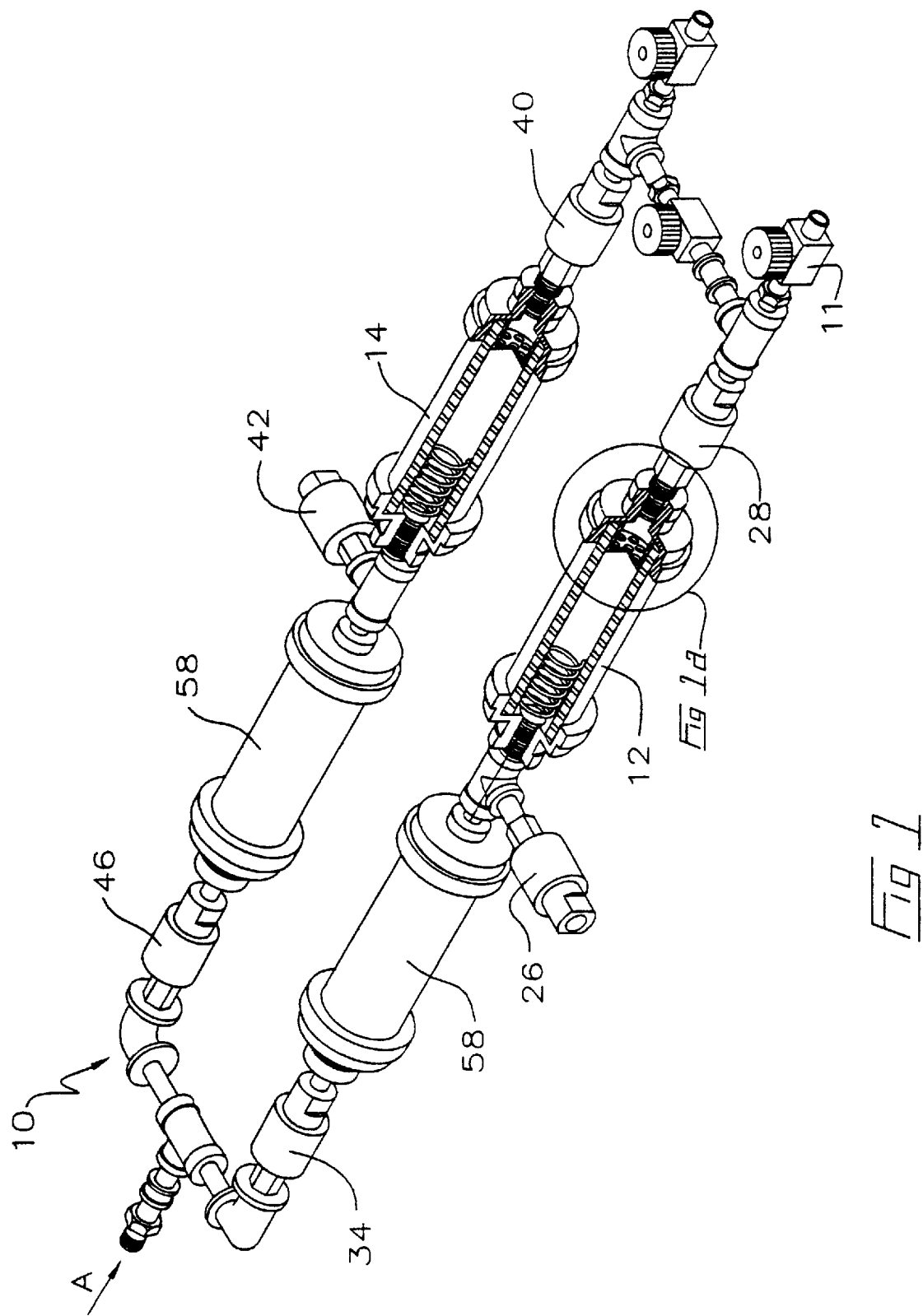

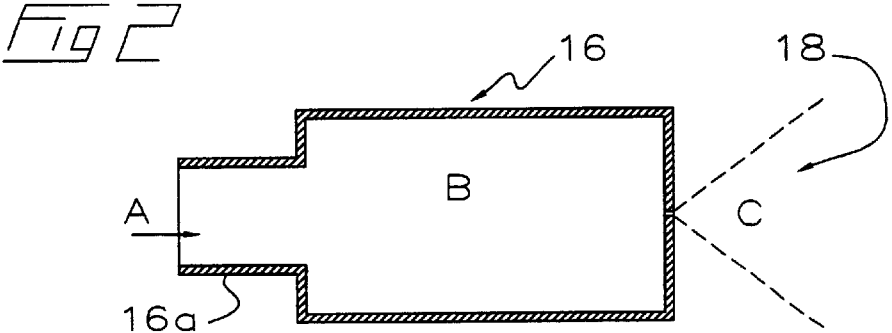
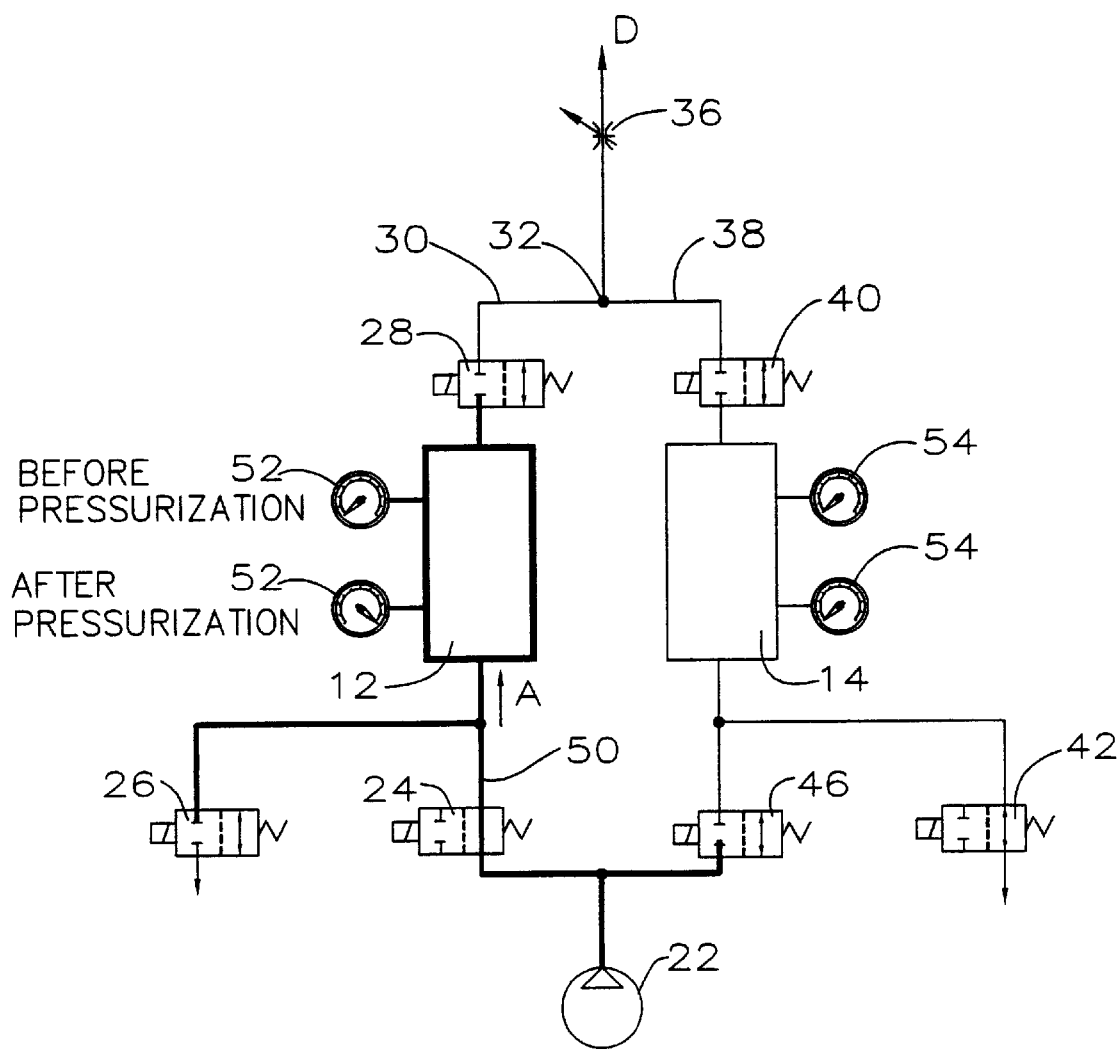

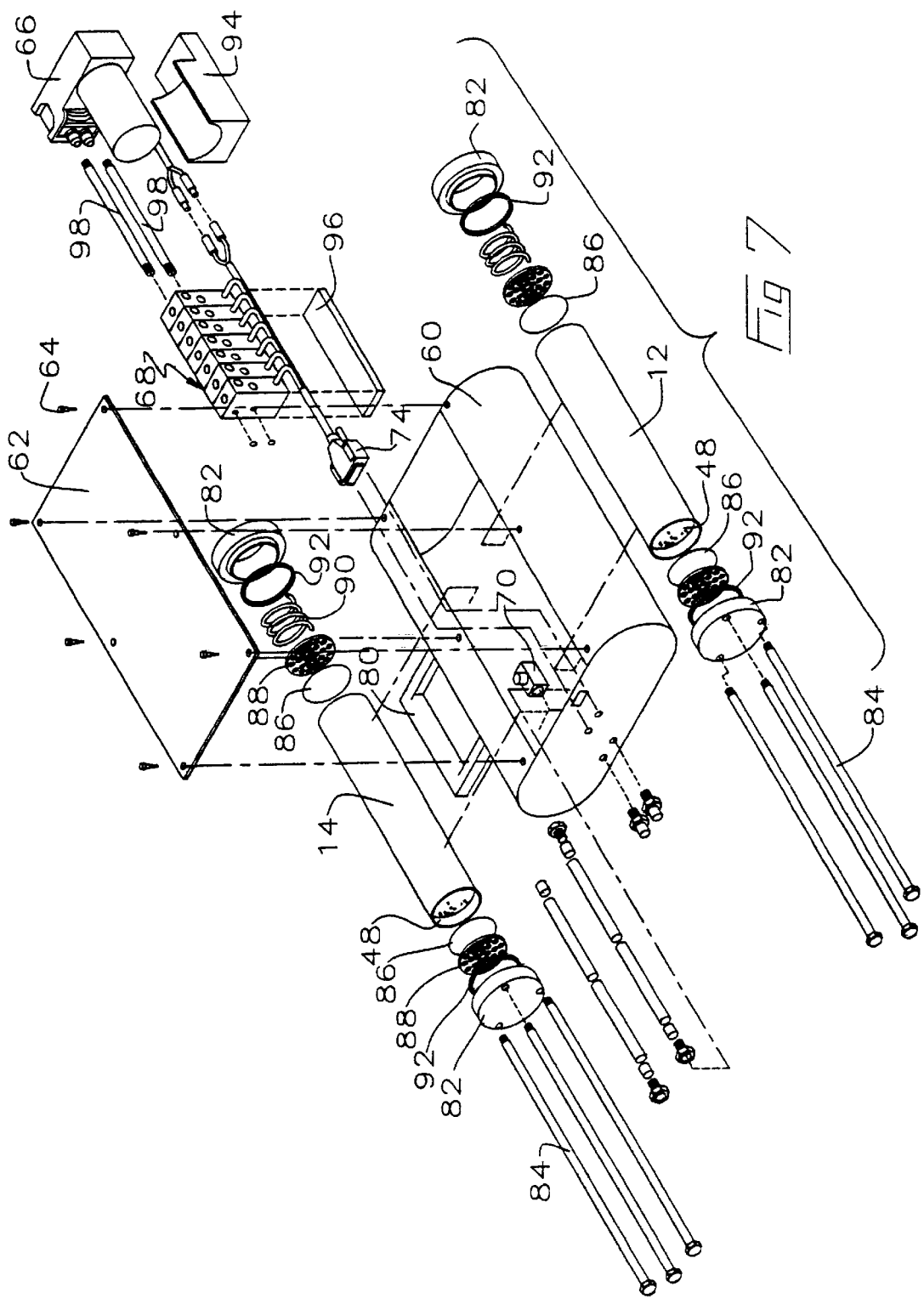

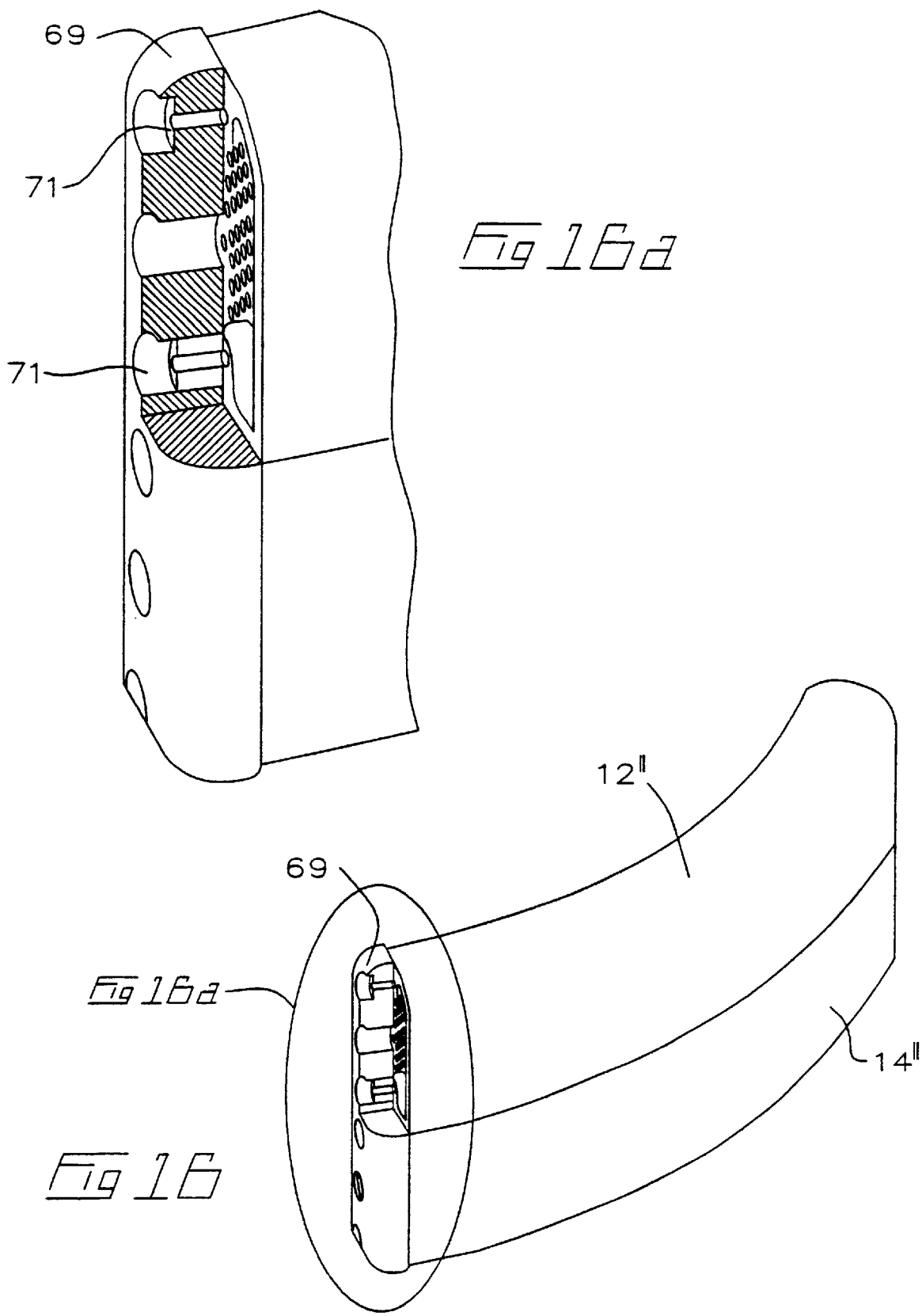

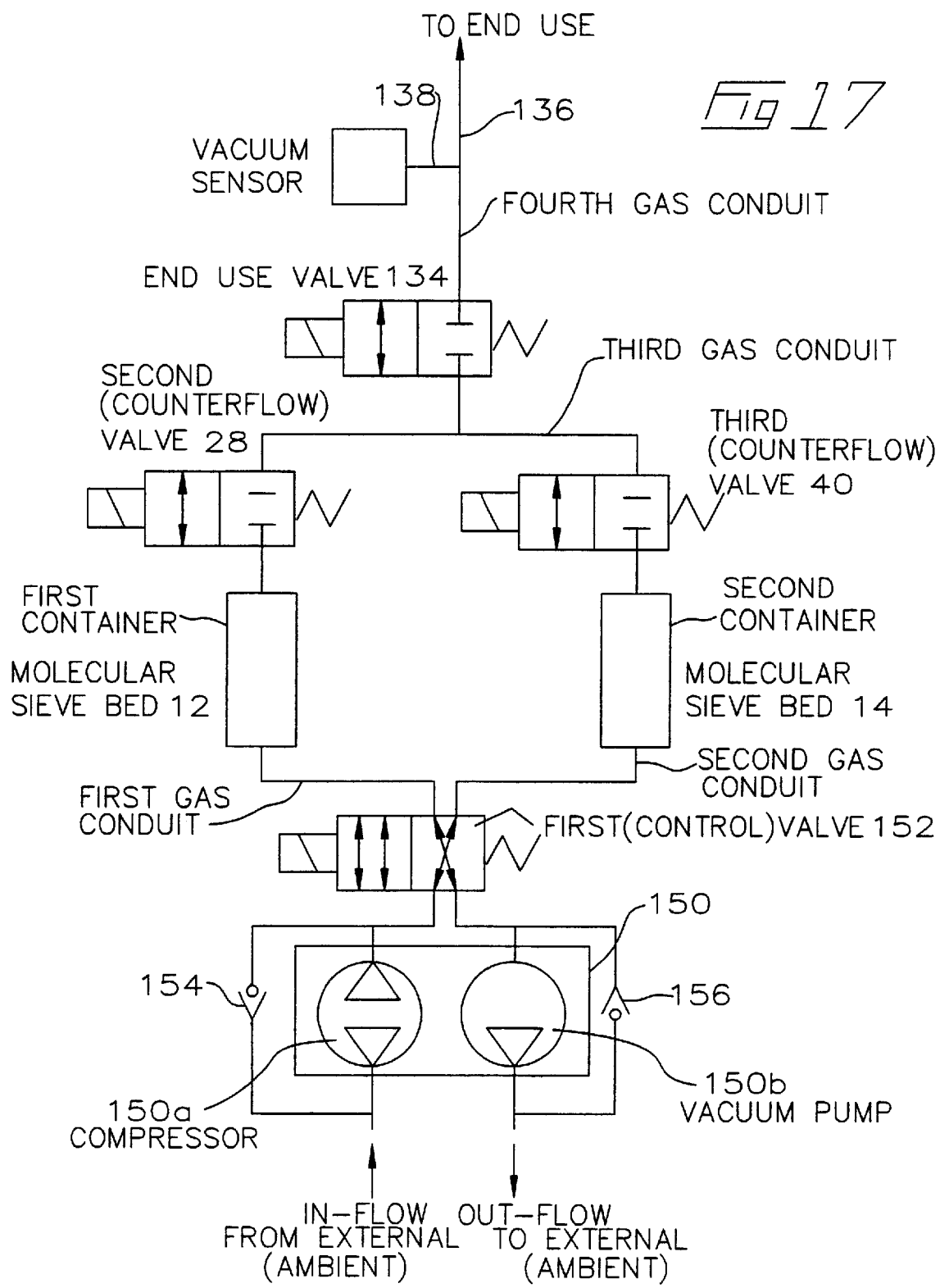

MINIATURIZED WEARABLE OXYGEN CONCENTRATOR

CROSS REFERENCE TO RELATED APPLICATION

This application is a Continuation-In-Part of U.S. patent application Ser. No. 09/921,863 filed Aug. 2, 2001 entitled Miniaturized Wearable Oxygen Concentrator, which claims domestic priority from United States Provisional Patent Application No. 60/222,591 filed Aug. 2, 2000.

FIELD OF THE INVENTION

This invention relates to the field of gas concentrators, and in particular to a miniaturized, portable gas concentrator and method of miniaturized gas concentration.

BACKGROUND OF THE INVENTION

The pressure swing adsorption cycle was developed by Charles Skarstrom. FIGS. 1A and 1B describe the operation of the Skarstrom "Heatless Dryer". In particular, ambient humid air is drawn into the system from an intake port, by a compressor. The pressurized air flows from the compressor through conduit 9 to a switching valve 4. With the valve in the shown position in FIG. 1A, pressurized air passes through conduit 5a to a pressure vessel 6a. The air feeds into the pressure vessel to a flow-restrictive orifice 1a. The effect of the restrictive orifice is to restrict the flow of gas escaping the pressure vessel. As the pressure builds up in the pressure vessel, water vapour condenses on the sieve material 8. Air with reduced humidity passes through orifice 1a to conduit 12. At conduit junction 11, some of the air is extracted for use from gas extraction port 2 while the remainder passes through conduit 13 to restrictive orifice 1b. The less humid air that passes through orifice 1b is used to blow humid air out of the unpressurized vessel 6b, through conduit 5b, through valve 4, to a vent port 7. When valve 4 switches to the position as shown in FIG. 1B, the opposite cycle occurs.

Thus, as valve 4 cycles from the position of FIG. 1A to the position of FIG. 1B, cyclically, there is a gradual reduction of humidity in the air as sampled at port 2. Likewise gases can be separated by adsorbing components of the gas on selective molecular sieves.

From laboratory observations, employing the Skarstrom cycle in the context of an oxygen separator or concentrator, wherein nitrogen is absorbed by molecular sieve beds to incrementally produce oxygen-enriched air, and using a precursor to the concentrator 1 arrangement of FIG. 1, it was observed that miniaturized (in this case nominal ¾ inch NPT pipe ×6 inch long) molecular sieve beds 12 and 14 could only reach a maximum of 30% concentrated or enriched oxygen detected at the gas extraction ports 11. It was thought that this was because the control valve of the laboratory arrangement was switching before all the nitrogen could be vented out of the molecular sieve beds and the exhaust lines. However, measurements showed that the oxygen concentration was higher than normal. Therefore this was not the problem.

It was also observed that there was a lot of airflow coming out of the molecular sieve bed before the molecular sieve bed was completely pressurized. It seemed that the molecular sieve bed was saturated with nitrogen before the bed was finished pressurizing. FIG. 2 diagrammatically represents such a molecular sieve bed 16. Compressed air enters the bed in direction A through inlet passage 16a. A volume of air B is contained within the bed cavity. A proportion of the volume of air C escapes out through an outflow needle valve 18 while the molecular sieve bed pressurizes. It was thought that the volume of air C escaping could be a much larger volume than the volume of air B inside the bed 16. Thus the question became, what happens when the volume of the molecular sieve bed is decreased during miniaturization, but everything else stays the same?

Poiseauille's Law was used in comparing the old bed volume B to the miniaturized bed volume to calculate the flow of a fluid that passes through a small hole such as needle valve 18 under a pressure difference.

$$1)\ Q = \frac{r^A (p_{InsideBed} - p_{OutsideBed})}{8\eta L}$$

Where "Q" is the fluid flow in meters cubed per second. "r" is the radius of the small hole. "$P_{InsideBed} - P_{OutsideBed}$" is equal to the pressure difference between inside the molecular sieve bed and outside the molecular sieve bed. "$\eta$" is the fluid viscosity, and "L" is the depth of the small hole.

The flow rate, Q, in meters per second multiplied by the time the flow rate occurred is equal to the volume of flow in meters cubed.

$$V = Qt \qquad\qquad 2)$$

The variable for Q in equation 1 in this case is constant so $$V = Kt \qquad\qquad 3)$$

where K is some constant value.

Using this information to create a comparison of the Flows and Volumes of the original oxygen concentrator's bed volume to the new bed volume may be described as:

$$4)\ R = \frac{\frac{V_{FlowNew}}{V_{BedVolumeNew}}}{\frac{V_{FlowOld}}{V_{BedVolumeOld}}}$$

Since the time to pressurize the molecular sieve bed can be accurately timed using a programmable logic controller (PLC) timer, the following can be stated:

$$5)\ R = \frac{\frac{Kt_{New}}{V_{BedVolumeNew}}}{\frac{Kt_{Old}}{V_{BedVolumeOld}}}$$

or $$6)\ R = \frac{\frac{V_{BedVolumeOld}}{Kt_{Old}}}{\frac{V_{BedVolumeNew}}{Kt_{Old}}} = \frac{\frac{V_{BedVolumeOld}}{t_{Old}}}{\frac{V_{BedVolumeNew}}{t_{Old}}}$$

The ratio may then be calculated by inserting values using representative values for a prior art bed and a miniaturized bed (in this case ¾ inch NPT×6 inch long). Thus, for example:

7) $R = \frac{(1)(0.001885741)}{(7)(0.0000434375)} = 6.2$

From this it was concluded that the molecular sieve material of a nominal ¾ inch NPT pipe×6 inch long molecular sieve bed (the example used in equation 7) has approximately 6.2 times the air passing through it during its pressurization cycle than the molecular sieve material of a prior art oxygen concentrator during its pressurization cycle.

As a consequence of the findings of this analysis it was found to be advantageous to pressurize and vent the molecular sieve beds in a different way than the prior art pressure swing adsorption (PSA) technique. In the method of the present invention the bed is mechanically evacuated after being substantially fully pressurized, hereinafter referred to as a gas packet system or method.

SUMMARY OF THE INVENTION

The gas, such as oxygen, concentrator of the present invention for enriching a target component gas concentration, such as the oxygen concentration, in a gas flow, includes an air compressor and vacuum pump, an air-tight first container containing a molecular sieve material for adsorbing a waste component gas such as nitrogen, and a second air-tight container containing molecular sieve material for adsorbing the waste component gas. The first container is in fluid communication with the compressor and vacuum pump through a first gas conduit, and the second container is in fluid communication with the compressor and vacuum pump through a second gas conduit. A third gas conduit connects the first and second molecular sieve containers in fluid communication with each other. A fourth gas conduit branches or "tees" off or otherwise cooperates, by means of a flow controller, with the third gas conduit to facilitate delivery of the target gas to the end use. For example, the flow controller may be mounted between two valves on the third conduit. A gas flow controller such as PLC or other dedicated electronic circuit controls actuation of valves mounted to the gas conduits. The electronically controlled valves may also work in co-operation with two passive one-way valves to regulate gas flow through the conduits so as to, in repeating cycles:

(a) prevent gas flow between the first and second containers and to allow compressed gas from the compressor into the first container during a first gas pressurization phase, whereby the first container is pressurized to a threshold pressure level to create a gas packet having an incrementally enriched target component gas concentration such as incrementally enriched oxygen-enriched air, while simultaneously evacuating the second container to a threshold vacuum level during a first evacuation phase whereby the second container is evacuated to the threshold evacuation level to remove a vacuum packet wherein a target waste gas such as nitrogen is removed from the molecular sieve of the second container and expelled to atmosphere, (b) prevent gas flow between either container and the compressor or vacuum pump and allow a regulated, that is defined or quantified amount of gas to flow from the first container into the fourth gas line for delivery of the target component gas such as oxygen enriched air for an end use by an end user, downstream along the fourth gas conduit, (c) prevent gas flow between either container and the compressor or vacuum pump or between either container and the end use, and allow a packet of enriched gas to flow between the first and second containers from the first container into the second container during an enriched gas packet flow phase, so that the enriched gas packet flows from the pressurized first container to the evacuated second container and, (d) prevent gas from flowing between the containers and pressurize the second evacuated container by for example simultaneously firstly exposing the second container to atmospheric pressure with a first one way flow control valve which allows the second container to pressurize to atmospheric pressure, that is ambient equilibrium, without use of the compressor; and then, secondly, actuating the compressor to continue to pressurize the second container after ambient equilibrium has been reached with atmospheric air pressure; and simultaneously preventing gas from flowing between the first and second containers while depressurizing the first container by for example simultaneously firstly venting the first container to atmospheric pressure through a second one way flow control valve to allow the first container to reach atmospheric pressure without the vacuum pump and, secondly, actuating the vacuum pump to evacuate the first container below ambient atmospheric air pressure.

The flow controller may be a gas flow splitter, for example a plug having a 0.0135 inch diameter hole, mounted to the third gas conduit for diverting a portion of the gas packet into the fourth gas conduit for delivery of target component gas, such as oxygen, enriched air for an end use, including use by an end user, downstream to the end use.

The gas flow controller may be a processor cooperating with the compressor and vacuum pump so as to shut off the compressor or vacuum pump when gas flow respectively between the compressor or vacuum pump and both the first and second containers is prevented by the valve actuation. The processor and the compressor and vacuum pump may be powered by a battery. The first and second containers, the conduits, the valves, the processor, the compressor and vacuum pump and the battery may be mounted in a housing.

The first and second containers may be elongate hollow conduits. The molecular sieve beds may, where the waste component gas is nitrogen, include Zeolite as the molecular sieve material. The first and second containers may be generally parallel and mounted in the housing in parallel array. They may be spaced apart laterally relative to the length of the containers so as to define a channel therebetween. The processor and the compressor and vacuum pump may be mounted in the channel. A valve and manifold housing may also be mounted in the channel, the valves mounted to the valve and manifold housing. The valve and manifold housing includes interconnecting manifolds for interconnecting the valves to the first and second containers and the compressor and vacuum pump via the gas conduits.

A gas reservoir may be provided, for example formed as part of the valve and manifold housing, in fluid communication with the gas flow splitter. The reservoir is for containing a reserve of, for example, the oxygen-enriched air for delivery to the end use. One of the valves is a demand valve cooperating between the gas line and the reservoir for release of the reserve into the gas line upon a triggering event triggering actuation of the demand valve. In one embodiment, a pressure sensor cooperates with the gas line, and the triggering event is a drop in pressure in the gas line sensed by the pressure sensor. The pressure sensor provides a triggering signal to trigger the actuation of the demand valve upon detecting the drop in pressure, for example to a pre-set lower threshold pressure, below which the pressure sensor provides the triggering signal.

In the embodiments in which the end use is for example oxygen supply to an end user such as a patient, the first and second containers may be elongate and curved along their length so as to conform to a body shape of the end user when the gas concentrator is worn by the end user. In any event, when the end use is oxygen supply to an end user, it is intended that the gas concentrator may be adapted to be worn by the end user.

Thus, the method of the present invention, for use with the gas concentrator described above, which may further include at least one selectively actuable first valve mounted to the first and second gas conduits, selectively actuable second and third valves mounted to the third gas conduit, the flow controller mounted between the second and third valves so as to regulate the cooperation between the third and fourth gas conduits, may be summarized as the steps of, advantageously sequentially, in repeating cycles:

(a) preventing the gas from flowing between the first and second container and allowing compressed gas from the compressor into the first container during a first gas pressurization phase, whereby the first container is pressurized to a threshold pressure level to create a first enriched gas packet having an incrementally enriched target component gas concentration, while simultaneously actuating the vacuum pump to evacuate the second container to a threshold vacuum level during a first evacuation phase whereby the second container is evacuated to the threshold evacuation level to remove a first waste gas packet whereby a target waste gas is removed from the second container and expelled to atmosphere, (b) preventing the gas from flowing between either of the containers and the compressor or the vacuum pump and allowing a regulated amount of the first enriched gas packet to flow from the first container into the fourth gas conduit for delivery of the target component gas for the end use, downstream along the fourth gas conduit, (c) preventing the gas from flowing between either of the containers and the compressor or the vacuum pump or between either of the containers and the end use, and allowing the first enriched gas packet to flow between the first and second containers from the first container into the second container during a first enriched gas packet flow phase, whereby the first enriched gas packet flows from the pressurized first container to the evacuated second container, (d) preventing the gas from flowing between the containers and actuating the compressor to pressurize the second container to the threshold pressure level to create a second enriched gas packet and simultaneously actuating the vacuum pump to de-pressurize the first container during a second evacuation phase and thereby remove a second waste gas packet whereby waste gas is removed from the first container and expelled to atmosphere, (e) preventing the gas from flowing between either of the containers and the compressor or the vacuum pump and allow a regulated amount of the second enriched gas packet to flow from the second container into the fourth gas conduit for delivery of the target component gas for the end use, downstream along the fourth gas conduit, and, (f) preventing the gas from flowing between either of the containers and the compressor or the vacuum pump or between either of the containers and the end use, and allowing the second enriched gas packet to flow between the first and second containers from the second container into the first container during a second enriched gas packet flow phase, whereby the second enriched gas packet flows from the pressurized second container to the evacuated first container.

The compressor and the vacuum pump may advantageously be a combined compressor/vacuum pump in a single unit so that the pressurization and evacuation are accomplished simultaneously by a single device.

The passive first and second one-way valves may be mounted in parallel to the compressor and the vacuum pump respectively so as to be in fluid communication with the first and second gas conduits when the compressor and the vacuum pump are respectively in fluid communication with the first and second gas conduits so that in-flow of gas from external to the concentrator during the first or second pressurization phase is simultaneously assisted by the first one-way valve, and so that out-flow of gas from the concentrator during the first or second evacuation phase is simultaneously assisted by the second one-way valve. Thus, during the first and second evacuation phases, the method may include firstly allowing de-pressurization to equivalent to the ambient pressure external to the concentrator through the second one-way valve and then actuating the vacuum pump to continue de-pressurization, and, during the first and second pressurization phases, firstly allowing pressurization to equivalent to the ambient pressure external to the concentrator through the first one-way valve and then actuating the compressor to continue pressurization.

BRIEF DESCRIPTION OF THE DRAWINGS

FIG. 1 is, in perspective view, a prototype embodiment of the oxygen concentrator of the present invention.

FIG. 1a is, in partially cut-away enlarged view, one end of a molecular sieve bed of FIG. 1.

FIG. 2 is a diagrammatic view of a singular molecular sieve bed having an uncontrolled outlet orifice such as would be found in the prior art pressure swing adsorption method.

FIG. 4 is a block diagram of a further embodiment of the oxygen concentrator of the present invention during pressurization of a first molecular sieve bed during an initial pressurization phase.

FIG. 7 is, in exploded perspective view, one embodiment of the oxygen concentrator of the present invention.

FIG. 8a is a cross-sectional view along line 8a—8a in FIG. 8.

FIG. 16 is, in partially cut-away perspective view, a further embodiment of the molecular sieve beds of the oxygen concentrator of the present invention.

FIG. 16a is, in partially cut-away enlarged view, one end of the molecular sieve beds of FIG. 16.

FIG. 17 is a further alternative embodiment of the block diagram FIG. 11.

DETAILED DESCRIPTION OF EMBODIMENTS OF THE INVENTION

Figure 1B:
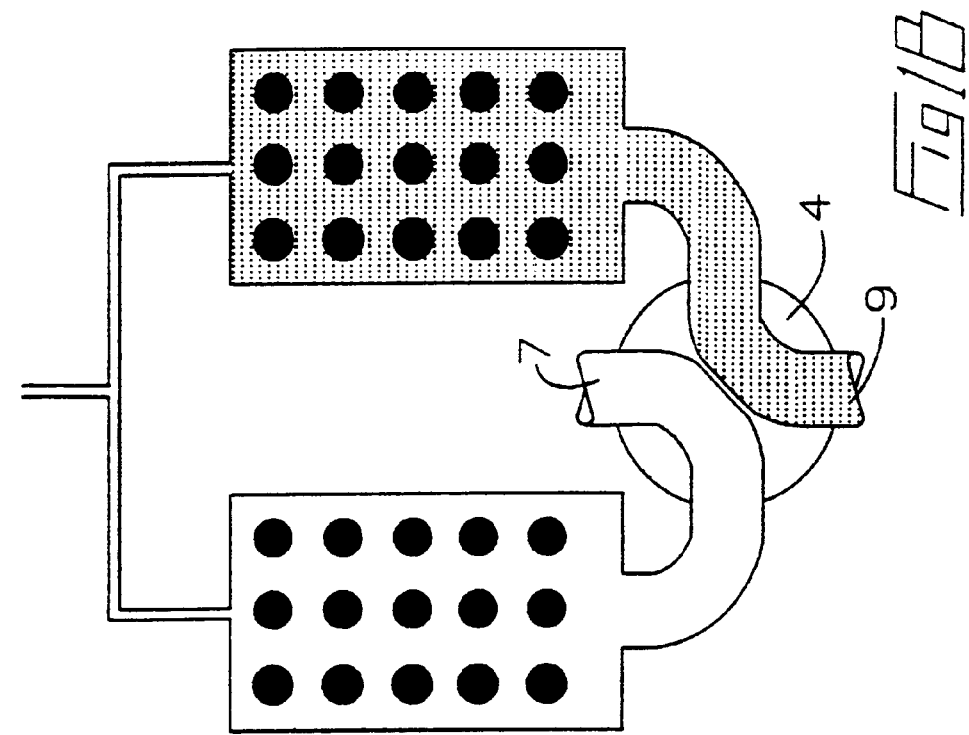
FIGS. 1A and 1B illustrate the Skarstrom Heatless Air Drying Device.

With reference to the accompanying figures in which like parts have the same reference numerals in each view, details of the concentration process and apparatus of the present invention are now provided. As used herein, including as used in the claims set out below, all references to oxygen and oxygen-enriched are intended to include other end-use gases which may be advantageously used in any end use once separated or concentrated according to the present invention from a parent gas (for example ambient air) comprising the end-use gas (for example oxygen) and waste gases (for example nitrogen) which may be adsorbed by a molecular sieve bed.

Figure 3:
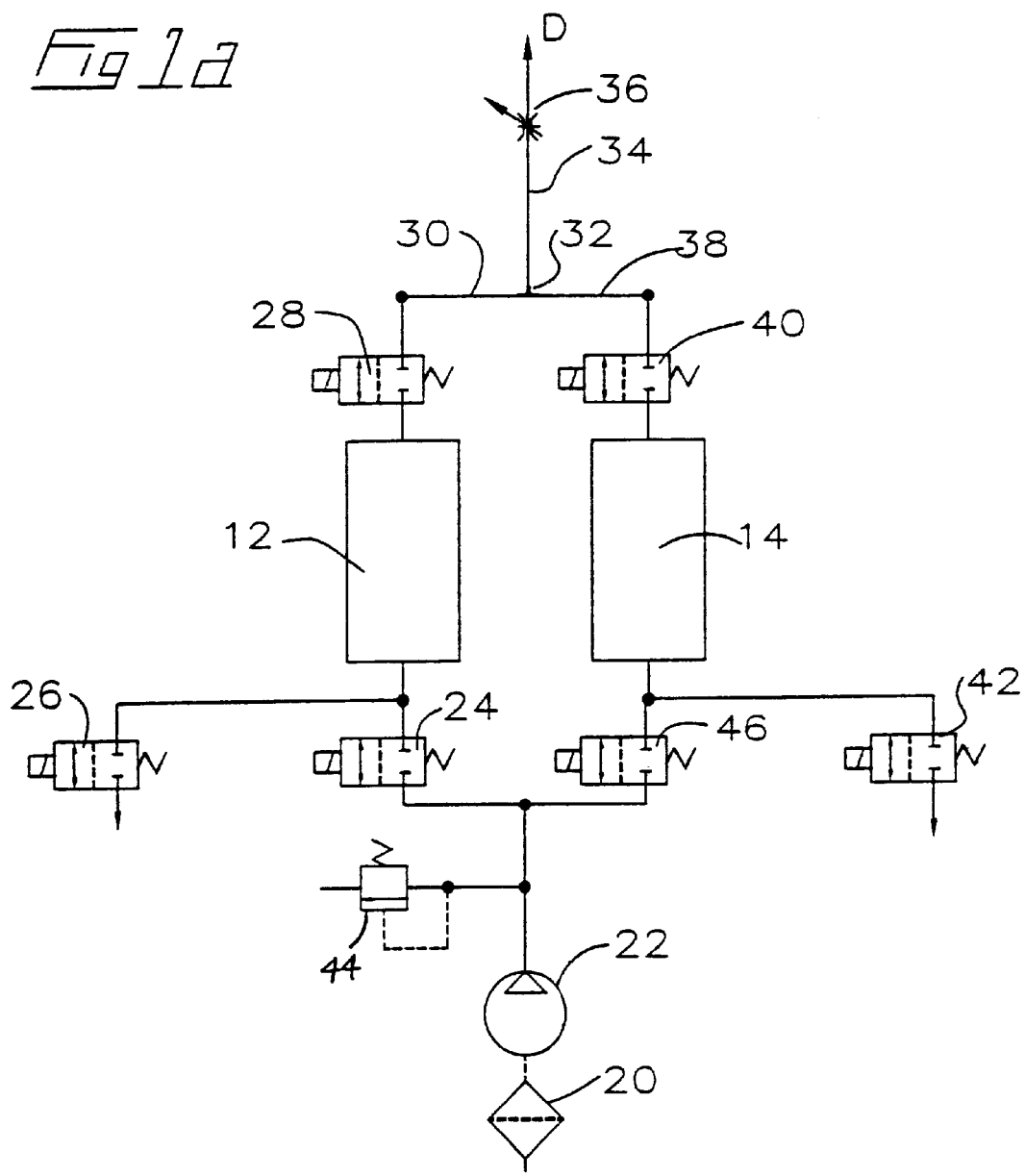
FIG. 3 is a block diagram of one embodiment of the oxygen concentrator of the present invention.
Figure 10:
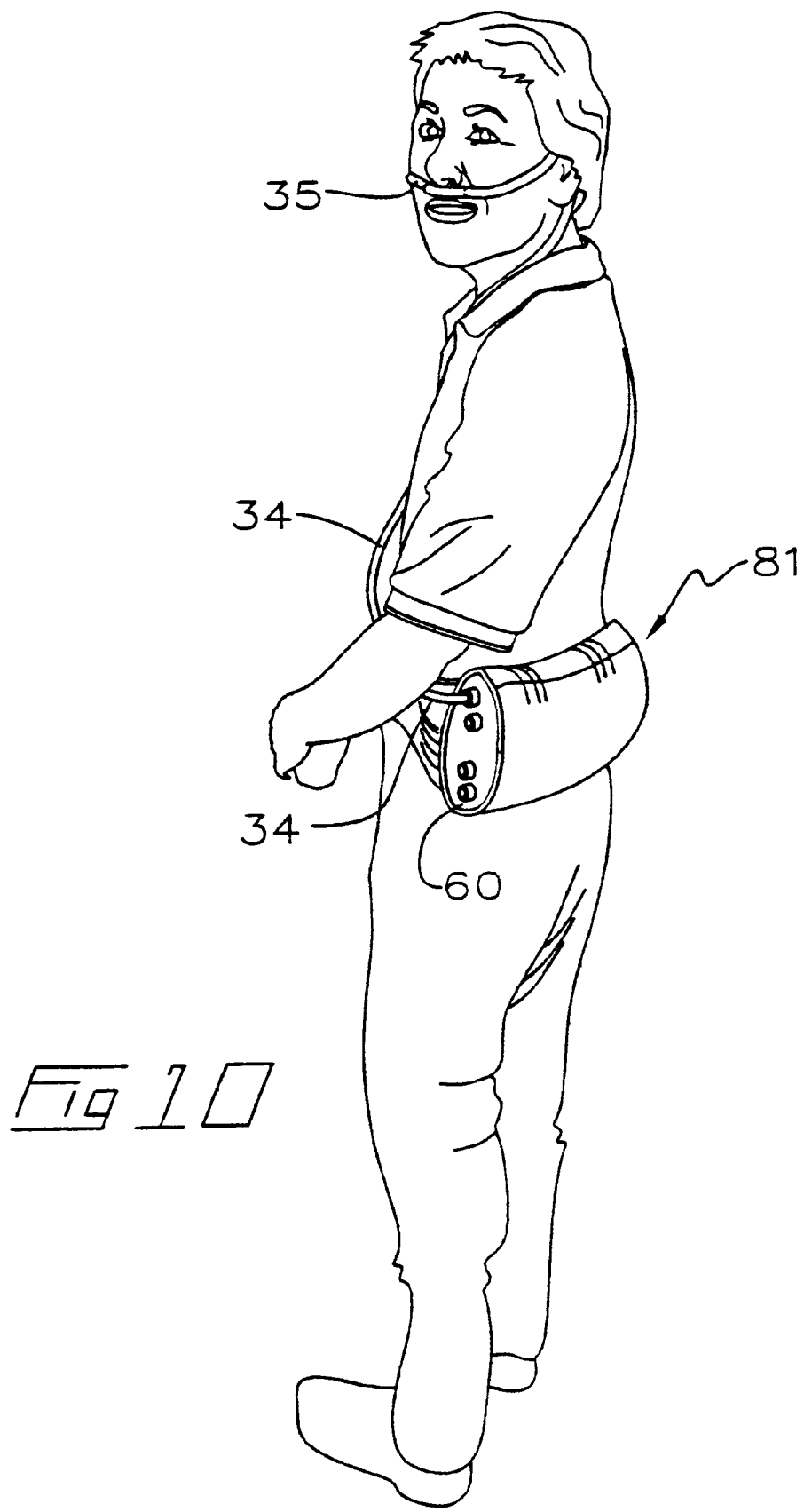
FIG. 10 is, in perspective view, an end user wearing an oxygen concentrator according to one embodiment of the present invention.

FIG. 3 is a diagrammatic illustration of an arrangement implementing the oxygen concentrator of the present invention. Air is filtered through intake filter 20 and is pressurized by compressor 22. The air stream is directed to pressurize bed 12 by having a supply valve 24 for bed 12 open and a nitrogen vent 26 for bed 12 closed. Control valve 28 is closed so that bed 12 pressurizes without any air venting. Valves 24, 26 and 28 may be solenoid valves. When bed 12 is pressurized, for example to 10 psi, then supply valve 24 is closed so that no more air enters into bed 12. At the same time control valve 28 is opened for a time to allow oxygen-enriched air to flow through air conduit 30 and the through air flow splitter 32 so as to split a percentage of the air flow through a gas extraction port and air flow conduit 34 so as to supply oxygen-enriched air to an end use at the end of conduit 34 such as a patient breathing the oxygen-enriched air flow. Conduit 34 supplies flow in direction D to an end-use (such as machine requiring or using oxygen-enriched air) or an end-user (such as seen in FIG. 10) through a needle valve 36. The remainder of the airflow continues through conduit 38 through open control valve 40 into bed 14 so as to be contained therein. Oxygen-enriched air that flows into bed 14 to purge the bed of nitrogen, vents out through the nitrogen vent 42. In an embodiment where the compressor is not turned on and off to preserve battery life, while bed 12 is generating oxygen-enriched air, pressure relief valve 44 may be venting air from compressor 22 unless the compressor is being run intermittently on a demand-based basis as better described below. Pressure may be relieved by the use of PLC time-controlled solenoid valves or pressure relief valves. It has been found advantageous to use 10 Angstrom Zeolite for example Oxi-sive 5™ (13x)Zeolite marketed by OUP in Calgary, Alberta, Canada, although as an example, and not intended to be limiting, other forms of Zeolite will also work.

Figure 5:
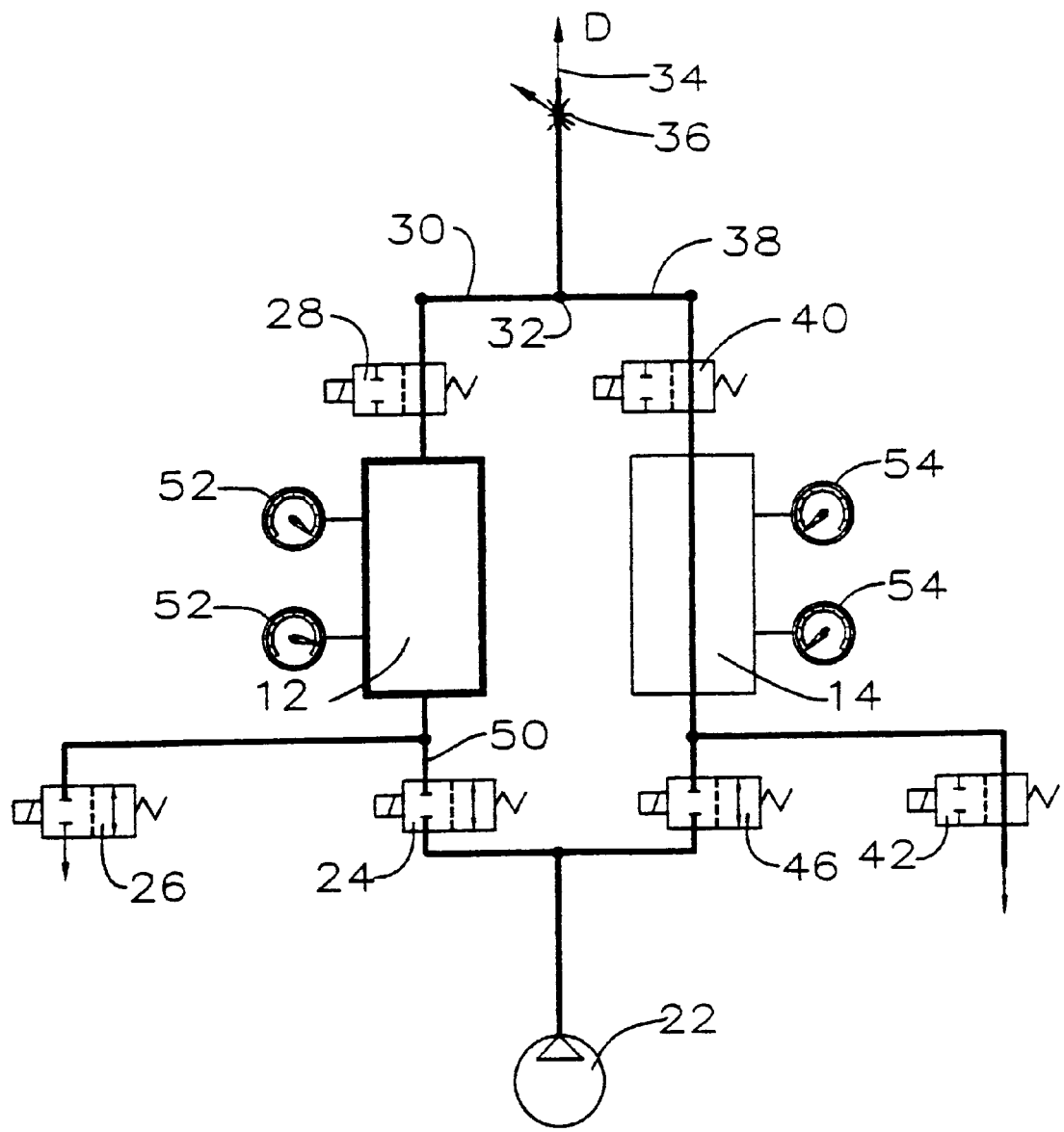
FIG. 5 is a block diagram of the oxygen concentrator of FIG. 4 during an air packet transfer phase.
Figure 6:
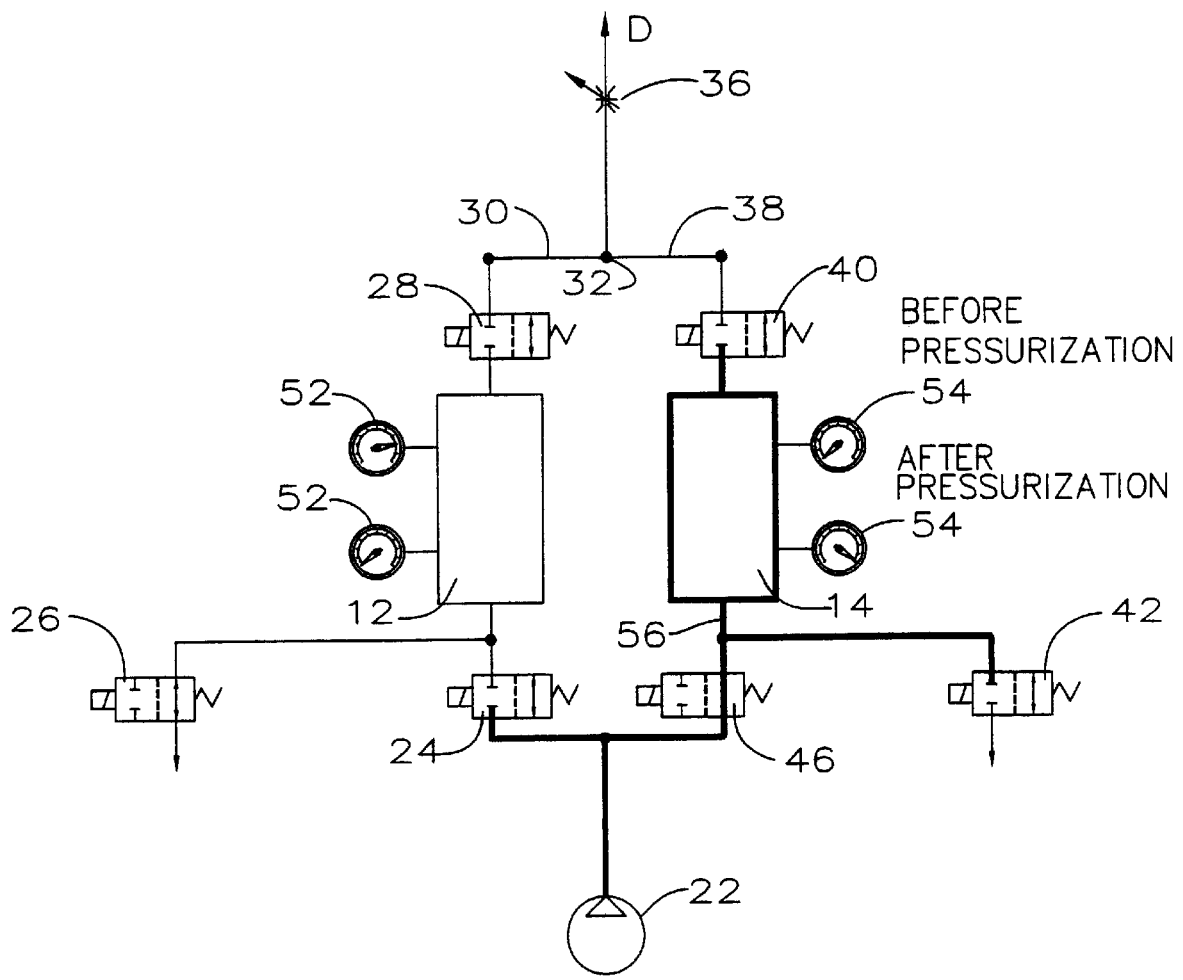
FIG. 6 is the oxygen concentrator of FIG. 5 during pressurization of a second molecular sieve bed.

The steps in concentrating oxygen are illustrated diagrammatically in FIGS. 4–6. The first step is to introduce ambient air into the inside of bed 12 (i.e. a chamber filled with Zeolite), then to pressurize bed 12.

Figure 1A:
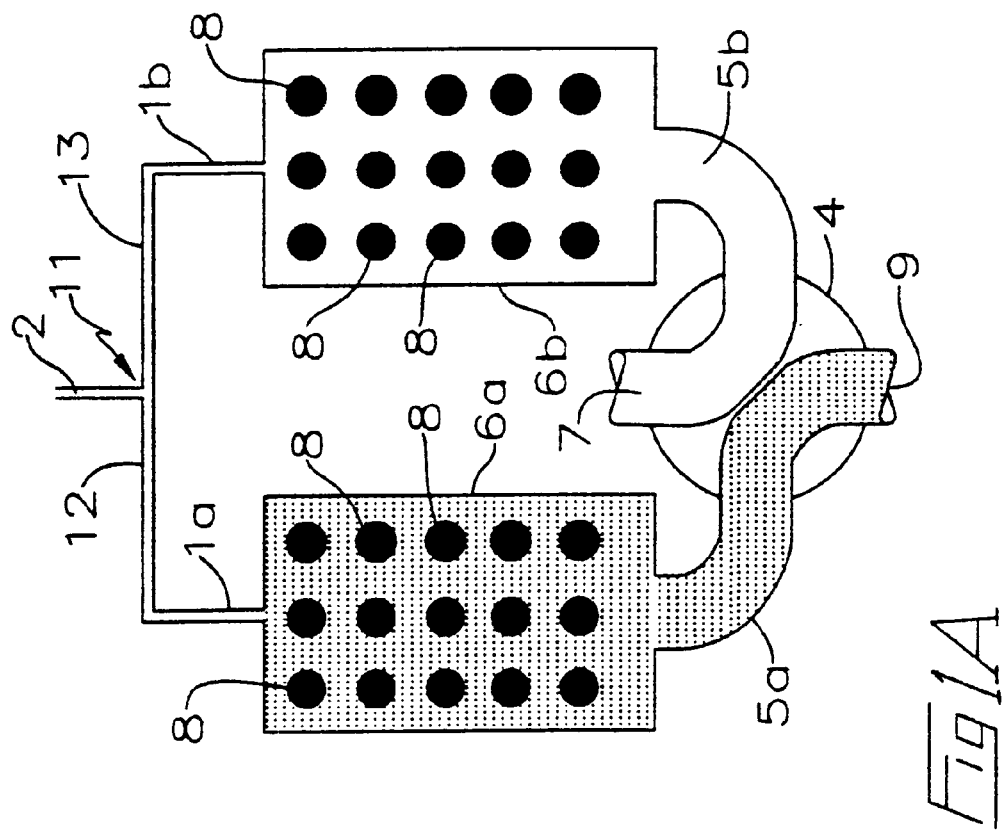
Figure 1A:
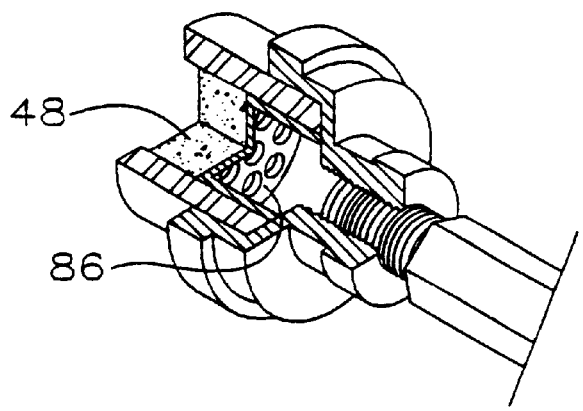

FIG. 4 illustrates pressurizing bed 12 for the first time. Herein the thickened and darkened air supply lines 50 and the darkened bed 12 indicate pressurized flow or pressurized static gas. The control valve 28, nitrogen vent bed 26 and supply valve 46 for bed 14 are closed, while supply valve 24 is open. At this point compressor 22 is introducing ambient air into bed 12 and pressurizing it. This continues until the bed reaches for example 10 psi as indicated by the pressure gauge 52. Next, supply valve 24 is closed and the pressurized air contained in bed 12 is separated into oxygen and nitrogen by the granular Zeolite molecular sieve material 48 better seen in FIG. 1a. At a molecular level the nitrogen is adsorbed by the Zeolite and held as long as the bed is under pressure. This leaves the oxygen-enriched gas within the pressurized chamber or cavity of the bed. It has been observed that this process occurs almost instantaneously. The pressure in bed 14 remains at ambient as indicated by pressure gauge 54.

Next, as shown in FIG. 5, control valve 28 is opened. The oxygen which had been separated within the chamber of bed 12 is the first gas to leave bed 12 as pressure is released through control valve 28. This oxygen-enriched air is fed from bed 12 into bed 14 through conduits 30 and 38. During this transfer some of the oxygen-enriched air is also released via splitter 32 through conduit 34 to the end-use or end-user as air flow in direction D, as regulated by adjustable needle valve 36. Splitter 32 and valve 36 may be a T-junction having a needle valve allowing for control of the split-off flow rate. As better described below, this may also be accomplished by a calibrated orifice controlling the split-off flow rate. As the oxygen-enriched air enters bed 14 it displaces the ambient air in bed 14 out of nitrogen vent 42. A net increase in the oxygen concentration contained within bed 14 results. The flow is discontinued before nitrogen is entered into the system to prevent a drop in oxygen concentration. For example, a bed initially pressurized to 20 psi, flow would be discontinued as the pressure drops to approximately 7 psi because nitrogen will start leaching into the air-stream at that point. In a larger industrial embodiment of the present invention, where the packet system of the present invention is employed for use with large beds, then oxygen or nitrogen sensors may be employed to detect when optimal oxygen concentration levels are reached (i.e. peaked) or to detect when nitrogen levels start to rise so as to control the flow and counter-flow duration. Such sensors may be installed for example adjacent the control valves, for example control valves 28, 40.

The process then repeats, but in the reverse order. As seen in FIG. 6, which shows the pressurization of bed 14, the oxygen-enriched air which had been introduced into bed 14 is contained by closing control valve 40 and nitrogen vent 42. Next, supply valve 46 is opened and compressor 22 begins to compress the oxygen-enriched air, again up to for example 10 psi through air conduits 56 into bed 14. Also, at this time control valve 28 and nitrogen vent 26 are opened to vent off the residual nitrogen from bed 12. Supply valve 24 is closed.

After the molecular sieve material 48 and gas contained within bed 14 are pressurized, control valve 40, control valve 28 and nitrogen vent 26 are opened. The oxygen-enriched air is then passed back into bed 12 from bed 14. As this air is introduced into bed 12 it assists in displacing the residual nitrogen from bed 12 out from nitrogen vent 26. After an optimized time, nitrogen vent valve 26 is closed along with control valve 28, and supply valve 24 is opened to start the cycle over again from the beginning.

The process of transferring or shunting oxygen-enriched air from one bed to another is known as, and hereinafter referred to as counter-flow. A reservoir 58 mounted upstream of the inlet for each molecular sieve bed may be employed to increase the counter-flow volume to volume-to-the-end-user gas flow ratio.

Figure 6A:
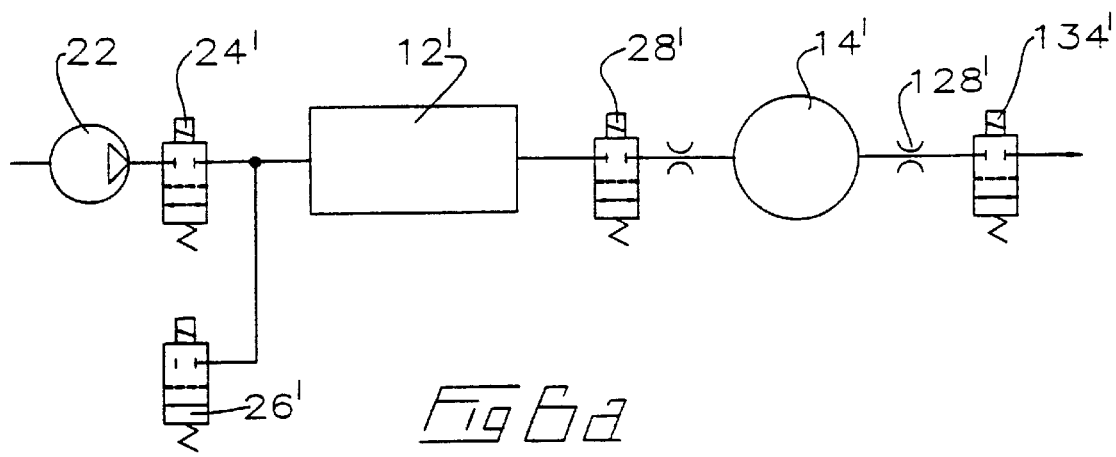
FIG. 6a is a block diagram of one embodiment of the oxygen concentrator of the present invention.

Alternatively as seen in FIG. 6a counter flow may be accomplished by use of only one molecular sieve bed 12' and one reservoir 14'. Compressor 22 pressurizes an airflow through valve 24' into bed 12'. Oxygen-enriched air is shunted through valve 28' from bed 12' into reservoir 14' instead of into a second bed, and then counter-flowed from the reservoir back into the bed using the packet airflow system of the present invention. This also accomplishes incremental increases per cycle in the oxygen concentration of the air packet being shunted back and forth from and to the bed so as to allow splitting or bleeding off to an end user of an oxygen-enriched air supply through orifice 128' and valve 134'. Nitrogen in bed 12' is purged or vented through valve 26'. In one embodiment a vacuum pump may be placed on valve 26 to evacuate bed 12' for enhanced gas separation. Alternatively the oxygen concentration according to the present invention may be accomplished by using a plurality of molecular sieve beds.

The counter-flow process is optimally timed to achieve an incremental increase in oxygen concentration per cycle. One way this is accomplished is by placing an oxygen concentration sensor on the end-user air flow conduit 34 and then, for example using an adjustable or otherwise regulatable splitter 32 to vary the percentage of air flow being diverted in direction D to the end-user, monitoring and regulating the percentage oxygen concentration in conduit 34. It has been applicant's experience that in this fashion a maximum percentage oxygen concentration passing through conduit 34 may be ascertained, and once found, the setting of splitter 32 has been correspondingly optimized. Once, for a particular arrangement, an optimized flow rate or valve setting has been ascertained, splitter 32 may be replaced with a non-adjustable flow splitter having a flow restrictor in the end-user gas flow line which is preset or pre-sized to replicate the optimized end-user gas flow rate. Applicant has found it advantageous when optimizing the counter-flow to start with excess counter-flow and then reduce the amount of counter-flow (decreasing the counter-flow time), for example starting with a counter-flow time equivalent to 75% of the time it takes to pressurize the beds to 10 psi. This is not to be taken, however, as implying that pressurization may only be done using a time-based method, as it is intended that the scope of this invention include using an air packet method which is pressure-based rather than time-based. That is, rather than pressurizing or depressurizing the beds for a preset time, it may be that the bed pressure is monitored and the air packet shunted upon a pre-set pressure threshold being met. Applicant has also found that using the method of the present invention, the size of the molecular sieve beds may be reduced from that presently found in the prior art, for example reduced to 75% of the size currently used in the prior art. Applicant has also found that using the method and apparatus of the present invention, that oxygen levels in the end-user gas flow line may reach in excess of 90%, with 95% oxygen levels thought to be sustainably available.

As seen in the embodiment of FIG. 7, molecular sieve beds 12 and 14 are contained within housing 60 in parallel spaced apart array so as to dispose the beds displaced laterally within the housing cavity thereby leaving a space between the beds running the length of the housing. This space between the beds may be accessed in one embodiment by removal of face plate 62 from housing 60, face plate 62 being releasably mounted to housing 60 for example by means of screw fasteners 64.

Figure 8:
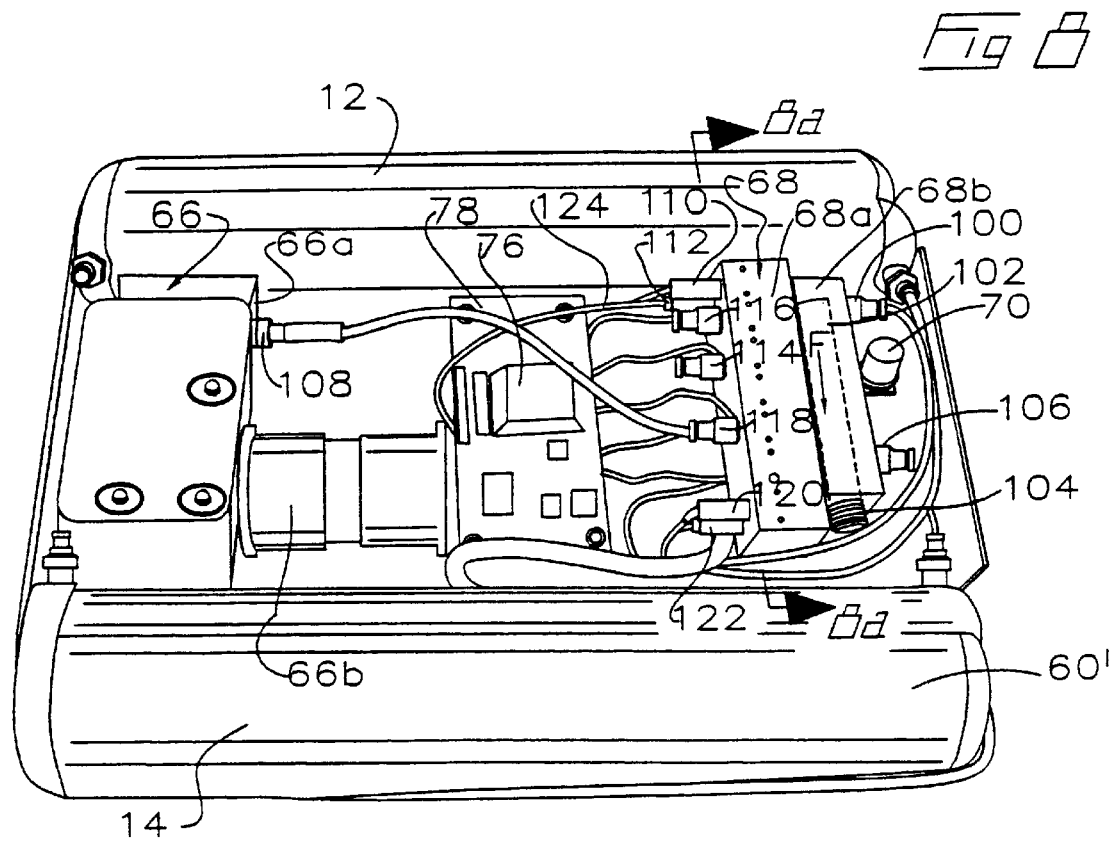
FIG. 8 is, in perspective view, a further embodiment of the oxygen concentrator of the present invention.
Figure 6A:
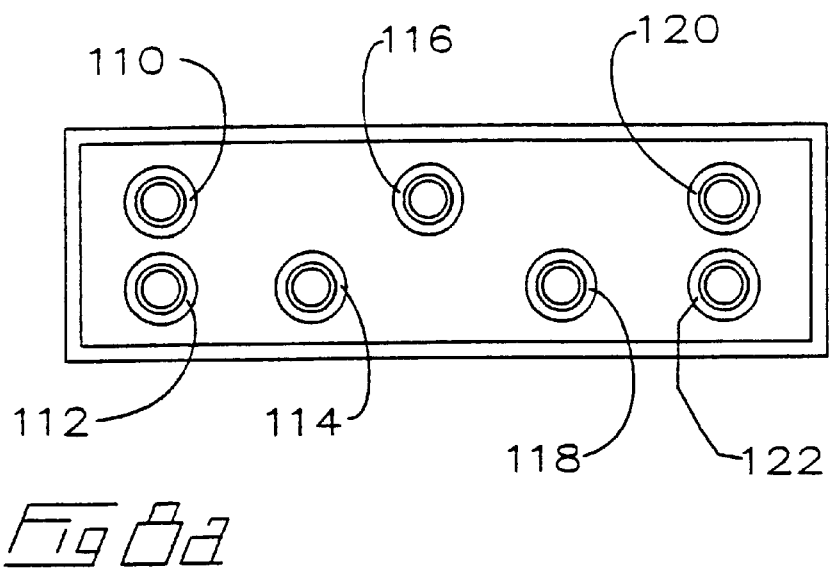
Figure 9:
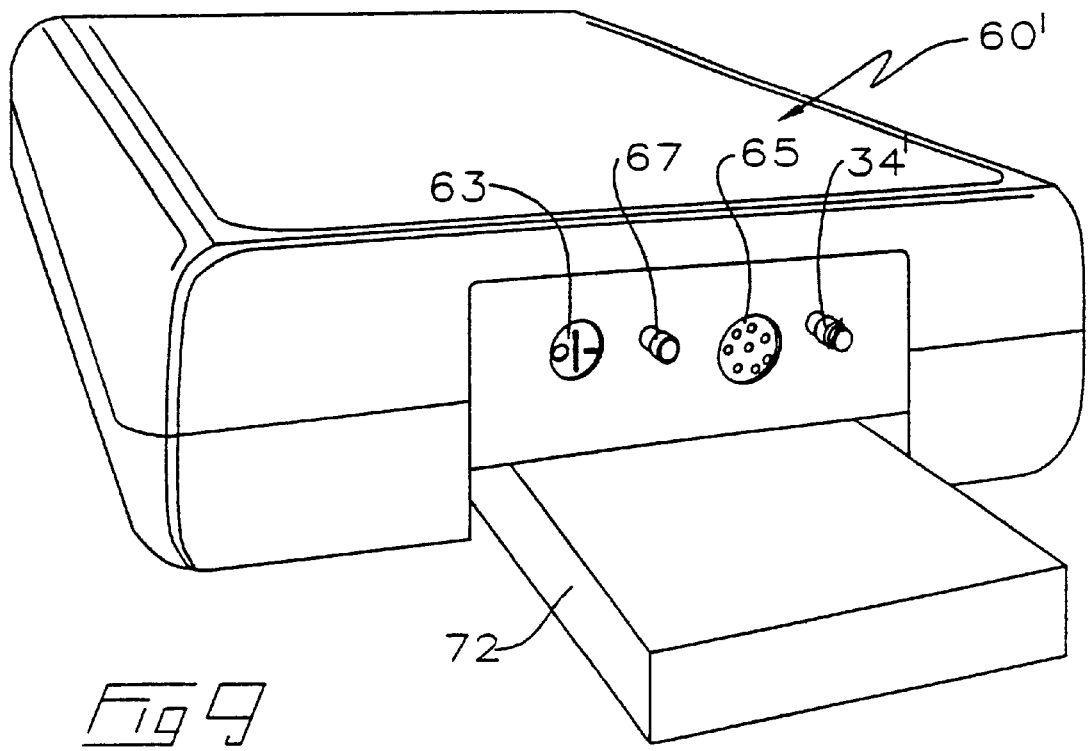
FIG. 9 is, in end-on perspective view, a housing according to one embodiment of the oxygen concentrator of the present invention.

Mounted between beds 12 and 14 within housing 60 are a compressor 66, a valve and manifold housing 68, a splitter valve 70 (to serve the function of splitter 32) and various flexible pipe or tubing to serve as the air conduits as better described below. The actuation timing of the valve actuation and the actuation timing of the compressor are controlled by signals from a PLC or other processor. In the embodiment of FIG. 7, the processor is remote from housing 60 and communicates via interface plug 74. In the embodiment of FIG. 8, which is otherwise substantially similar to that of FIG. 7, the remote PLC or processor is replaced with an onboard PLC or processor 76 mounted on circuit board 78, where circuit board 78 is mounted between compressor 66 and valve housing 68. Also, in the embodiment of FIG. 8, faceplate 62 is replaced with a one-half clam shell style cover (not shown), that is, the housing is formed as a clam shell cover arrangement as better seen in FIG. 9 and labeled as housing 60'. An end mounted control panel may contain an on/off power switch 63, an air extraction port 34' a perforated air intake plate or grate 65, and a 12 volt DC connector 67.

Housing 60' may have a handle 80 mounted along one lateral side for carrying of the oxygen concentrator of the present invention, it being understood that providing for hand-held carrying is not intended to be limiting. The present invention is also intended in alternative embodiments to be worn by a user, for example in or as a backpack or hip pack or so-called fanny pack 81 such as seen in FIG. 10. Conduit 34 extends from the housing to the end-user so that, where the end-user is a patient requiring a supply of oxygen-enriched air, conduit 34 may supply nasal tubes 35 as commonly in use in the prior art.

In the embodiments of FIGS. 7 and 8, beds 12 and 14 may be 2 inch inside diameter pipe, having a length of approximately 12 inches so as to provide for carrying therein molecular sieve material having a length of, in one embodiment, 9 and ½ inches although applicant has obtained high concentrations with a smaller molecular sieve bed size. The beds are sealed on their ends by end caps 82, suitably bored or otherwise ported so as to cooperate with air conduit tubing forming the pneumatic circuit (not shown in FIG. 7 for clarity) and to allow for the fastening of the end caps onto the ends of the bed pipes for example by the use of elongate bolts 84 as seen in FIG. 7. The Zeolite molecular sieve material 48 is sandwiched longitudinally within the cylindrical pipe housing of each bed between a pair of porous membranes 86, themselves sandwiched between a pair of porous backing plates 88. The sandwich of porous backing plates 88, porous membranes 86, and molecular sieve material 48 may be resiliently urged to one end of the bed by a resilient biasing means such as helical spring 90. The porous membranes 86, which may be felt porous backing material or other material to contain material of the molecular sieve bed from passing through the openings of porous backing plates 88, are sized to cover the entire opening within the cylindrical beds. Porous backing plates 88 may be rigid plates having holes drilled there through. The end caps 82 may be sealed onto the ends of the piping forming the bed housings by means of O-rings 92.

Compressor 66, which may be a Thomas™ 8009DC compressor having its mounting plate removed and adapted to rotate the head ports by 180 degrees, or a Thomas™ 7006 series compressor as depicted in FIG. 8, may be mounted into housing 60 by means of a resilient mounting plate 94 which may be of open cell high density foam or Sorbothane™ or other dampening material. A further resilient mounting plate 96, which may also be of open cell high-density foam may be employed to mount valve housing 68 into housing 60. In the embodiment of FIG. 7, valve and manifold housing 68 includes a series of Seven Humphrey™ 310 series 24 volt DC direct acting valves bolted into side-by-side adjacent array by means of elongate bolts 98. As depicted in FIG. 8, the valves may also be Humphrey™ HK5 valves.

Valve and manifold housing 68 has an array of valves mounted adjacently as a block 68a, and conveniently disposed along the back side of the block is a reservoir and muffler manifold 68b. Air conduits lead into the muffler cavity, which may be a bore formed in manifold 68b and filled with sound-dampening material, for example cellulose fibre, and a conduit leads from the muffler to the compressor so as to supply air to the compressor. Further conduit then leads from the compressor into the valve block 68a so as to supply compressed air to the supply valves. Thus as seen in FIG. 8, coupler 100 and its corresponding air conduit draw air from outside of the housing and feed it into muffler 102 shown in dotted outline. Muffler 102 may be accessed through end cap 104, which may be threadably mounted into the end of the muffler bore.

Air from the air intake coupler 100 passes through muffler 102 in direction F so as to exit through the muffler output coupler 106 and its corresponding air conduit which feeds air into the compressor 66, and in particular, into the compressor cylinder head 66a. Upon compression of the air by the operation of the compressor cylinder contained within the compressor/vacuum pump cylinder head housing 66a by the operation of motor 66b, air is compressed and output through compressor output coupler 108 and its corresponding air conduit.

Figure 11:
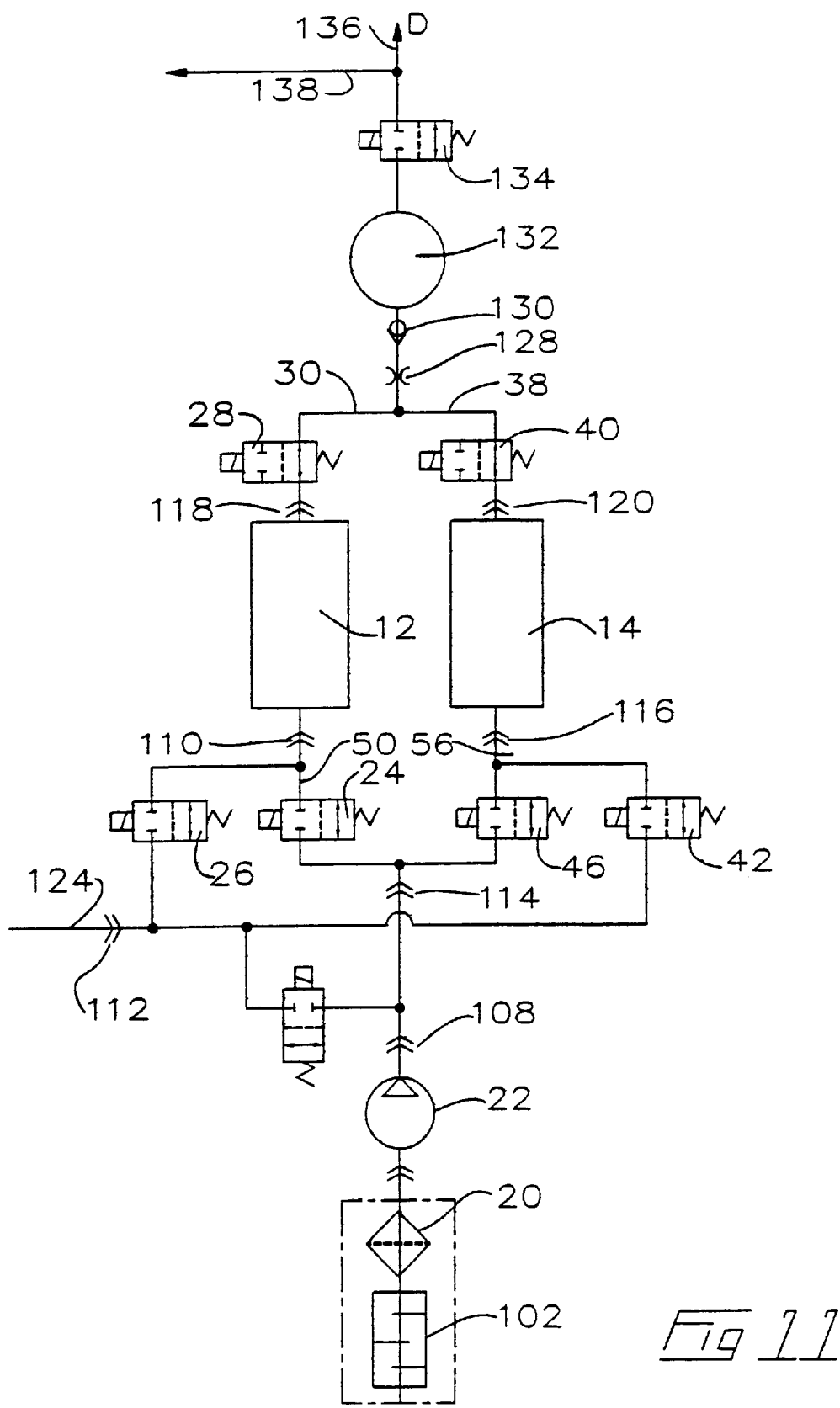
FIG. 11 is a block diagram of a further embodiment of the oxygen concentrator according to the present invention.
Figure 12:
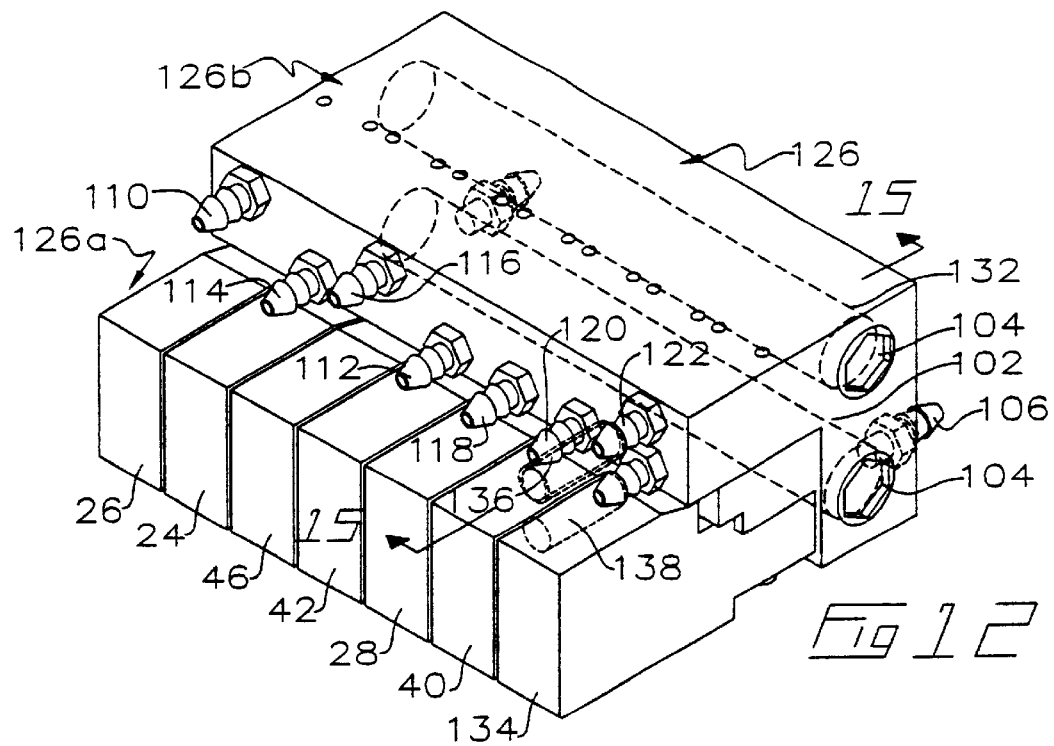
FIG. 12 is, in perspective view, a valve and manifold housing according to one embodiment of the oxygen concentrator of the present invention.
Figure 13:
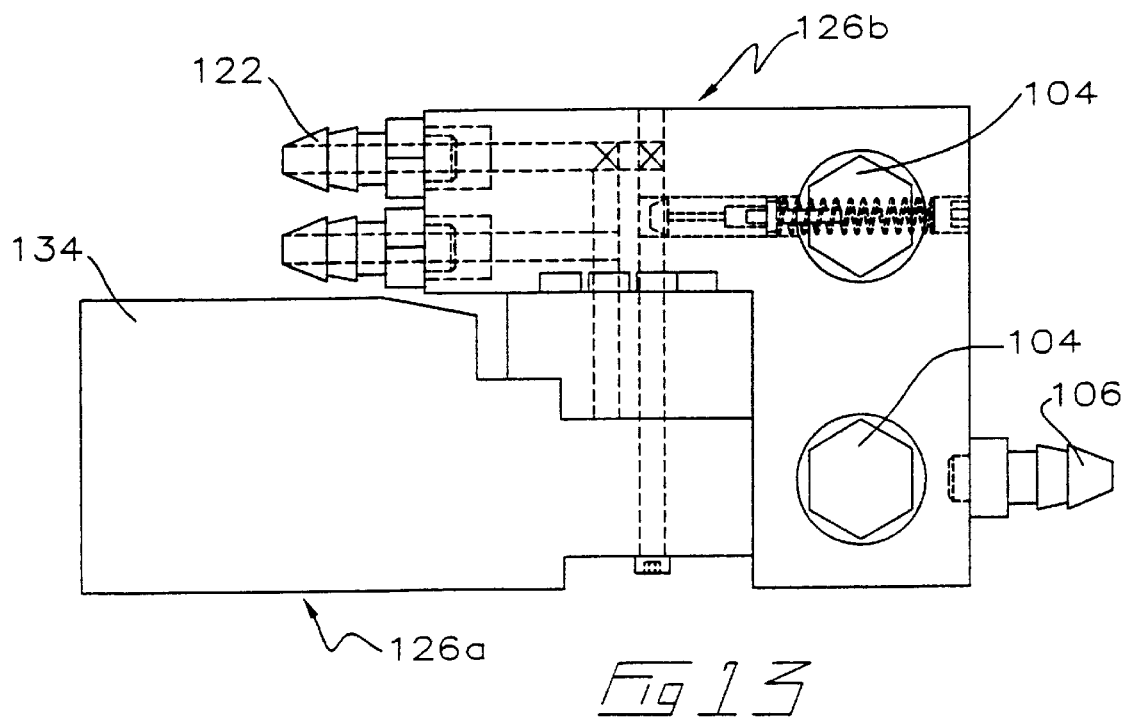
FIG. 13 is, in side elevation view, the valve and manifold housing of FIG. 12.
Figure 14:
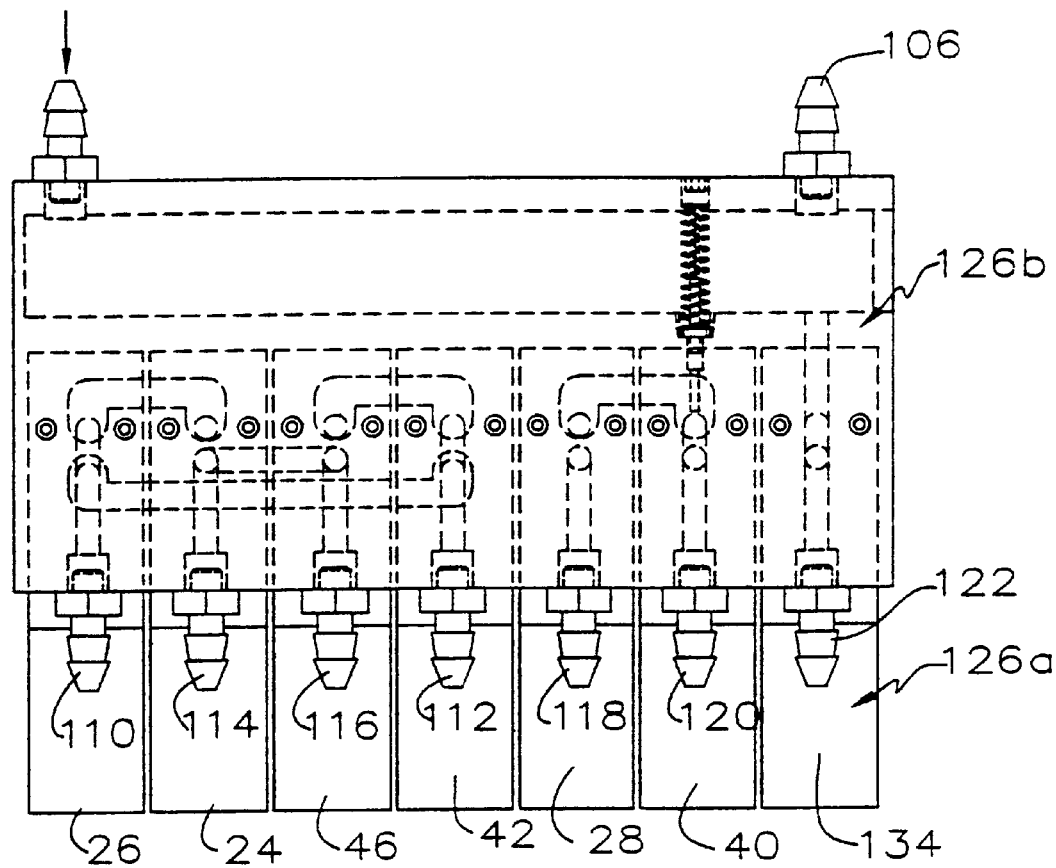
FIG. 14 is, in plan view, the valve and manifold housing of FIG. 13.
Figure 15:
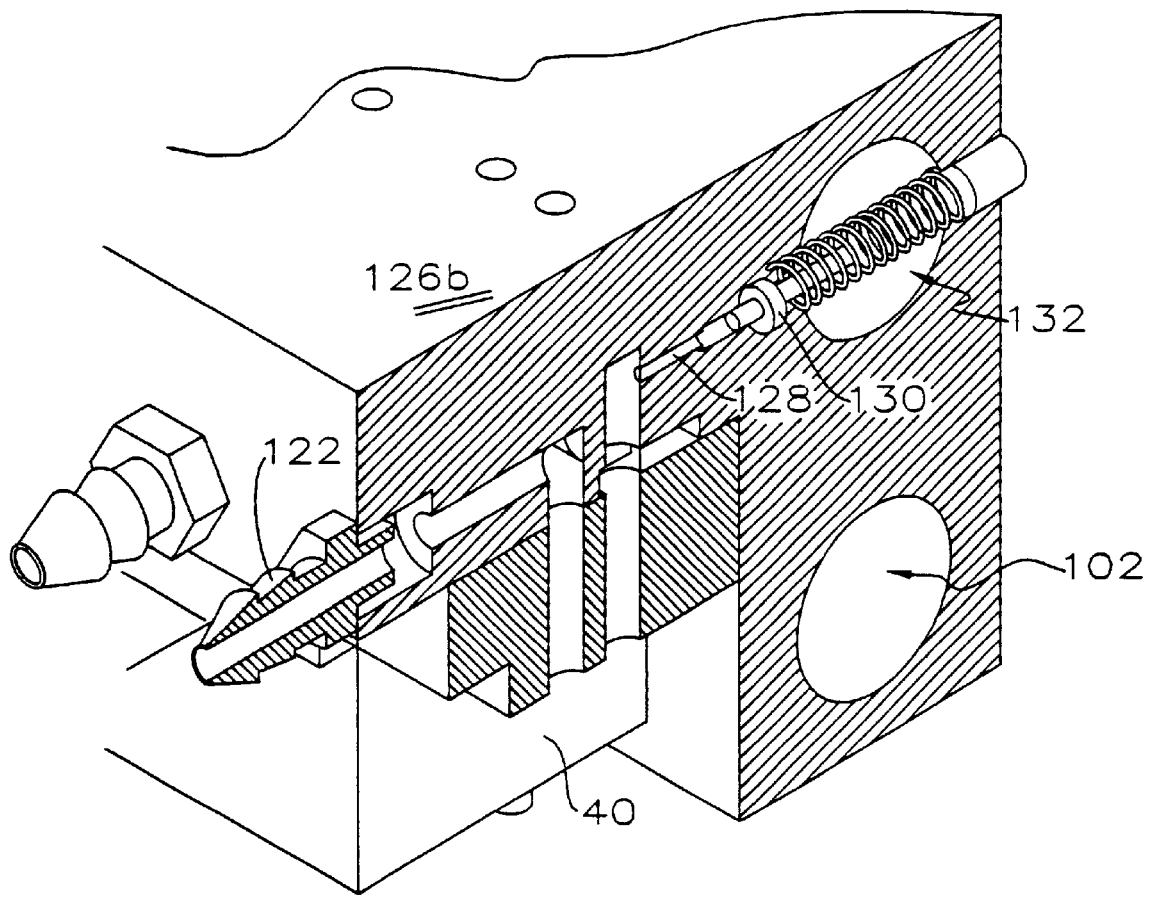
FIG. 15 is a cross-sectional view along line 15—15 in FIG. 12.

As better seen in FIG. 8a, which illustrates the front face of valve block 68a, seven air conduit couplers are provided. Without intending to be limiting in their arrangement, they are the bed 12 infeed coupler 110 between supply valve 24 and bed 12, the common nitrogen vent coupler 112 which commonly vents from both nitrogen vent 26 and nitrogen vent 42, the compressed air infeed coupler 114 from compressor 22, the bed 14 infeed coupler 116 between bed 14 and supply valve 46, the bed 12 outfeed coupler 118 between bed 12 and control valve 28, bed 14 outfeed coupler 120 between bed 14 and control valve 40, and the patient air flow coupler 122. These couplers are illustrated in the diagram of FIG. 11 which also illustrates the common venting of nitrogen vents 26 and 42 through vent line 124 and the removal of the pressure relief valve of FIG. 3 as being unnecessary due to the switching on and off of compressor 22. FIG. 11 also illustrates features of an alternative embodiment for valve and manifold housing 68, and in particular valve and manifold housing 126 as illustrated in FIGS. 12–16.

FIG. 11 also illustrates a further embodiment of the oxygen concentrator of the present invention. Rather than using an adjustable flow splitter 32 or an adjustable needle valve 36, the proportion of oxygen-enriched air flow flowing in direction D through conduit 34 is regulated by a pre-set optimized orifice 128 which then flows through a check valve 130 into reservoir 132. Outflow from reservoir 132 is controlled by demand valve 134. The air flow then may split between air flow to the patient along conduit 136 and air flow to a pressure sensor (not shown) along conduit 138. The sensor on conduit 138 may then be employed to sense when a patient is demanding a surge release of oxygen-enriched air from reservoir 132. Thus when the patient creates a drop in pressure in conduit 136 such as would be caused by suction applied to conduit 136, the sensor detects the drop in pressure below a pre-set threshold and causes the processor to trigger the release of the reserve of oxygen-enriched air contained within reservoir 132. In alternative embodiments, the reservoir may be large enough to contain a sufficient supply of oxygen-enriched air for more than one inhalation on demand by the patient through demand valve 134. The embodiment of FIG. 11 is also reflected in FIGS. 12–16 which illustrate a bored reservoir 132 bored into the manifold block 126b parallel to muffler 102. As with the muffler, the reservoir may be bored and sealed using a threaded end cap 104.

In another embodiment, a portion of the product gas from a first or generating container such as bed 12 is delivered to a second or regenerating container such as bed 14 by opening valves 28 and 40, while keeping valve 134 closed. When bed 14 has received the desired volume of flow of enriched gas, valves 28 and 40 close. Now the container or bed 12 contains a large volume of enriched gas in storage to be delivered for end use as the sensor attached to conduit 138 determines. Delivery occurs by keeping valve 40 closed and opening valve 28 and 134 for a period of time.

In this embodiment, the flow restrictor 128, the directional control valve 130, and the reservoir 132 as in other embodiments need not be employed. In the reverse, when the container or bed 14 is under pressure and ready to be employed for gas generation, a portion of the product gas may be delivered to the container of bed 12 (now the regenerating container) from the generating container of bed 14 by opening valves 28 and 40, while keeping valve 134 closed.

When the container of bed 12 has received the desired flow of enriched gas, the valves 28 and 40 close. Now the container or bed 14 contains a large volume of enriched gas in storage to be delivered for end use as the sensor attached to conduit 138 determines. Delivery occurs by keeping valve 28 closed and opening valve 40 and 134 for a period of time.

Applicant has observed that the molecular sieve material may allow 3 times the volume of gas to be stored under pressure as the same volume of an empty container (i.e. without sieve material) under pressure. This property of storing increased volumes of compressed gas has further applications than the oxygen concentration application. Increasing the volume of gas which may be stored under pressure in a standard pressure vessel has application in for example such diverse areas as scuba diving, gas welding and storage, gas-fueled automobiles and other devices.

As seen in FIGS. 16 and 16a, it is intended to form part of the scope of the present invention that the molecular sieve beds 12" and 14" may be curved rather than linear. For example, the beds 12" and 14" may be curved along their length so as to better conformally fit about the waist of a user wearing them such as in FIG. 10. End plates 69 may be bolted through bolt holes 71 to the frame or casing of the housing or beds respectively to seal the ends of the beds. The beds may be formed as a curved adjacent parallel pair of beds such as seen in FIG. 16 or, consistent with the previously described embodiments, be laterally spaced apart and parallel within a housing which would also then have a correspondingly curved surface to facilitate ease and comfort of wearing the oxygen concentrator of the present invention. In all such wearable embodiments, it may be that control switches such as the "on/off" switch, the air intake, the enduser air flow outlet and the like are mounted within the carrying media, such as a back pack, fanny pack etc., so as to be exposed from one end of the housing and from one side of the carrying media. Thus as seen in FIG. 10 the user has ease of access to the control functions and to the air flow outlet from which the air flow conduit extends for use.

FIG. 17 shows an alternative embodiment in which a combined compressor/ vacuum pump 150 (which may be a separate compressor 50a and vacuum pump 150b) is in communication with a direction-reversing valve 152, which selects which container of beds 12 or 14 is pressurized and which is evacuated. The containers of beds 12 and 14 (that is the containers that contain the gas separating sieve material 48) are in fluid communication with valves 28 and 40 respectively. Valves 28 and 40 are in fluid communication with valve 134. A sensor conduit 138 is in communication with conduit 136 which supplies enriched gas for end use. The operation of this embodiment is similar to the operation of the embodiment of FIG. 11, except for the addition of the vacuum pump 150b to enhance operation. The vacuum pump is used to extract gas from the regenerating container (be it either the container of bed 12 or 14) rather than having the gas vent to ambient atmosphere. Flow direction control valves 154 and 156 reduce the compressive energy requirements by 50% as the direction-reversing valve 152 is switched.

An end user may require an oxygen generator that produces greater than 90% oxygen. The preferred embodiments of the present invention may deliver 425 milliliters of oxygen per minute, as an end-user patient demands it by inspiration, and may take no more than seven seconds to pressurize a molecular sieve bed to attain proper flow rates.

During testing applicant has determined that, during one cycle, a pressurized sieve bed produces high concentrations of oxygen exceeding eight liters per minute for one second, (133 milliliters per second). This is enough oxygen for five breaths at 25 milliliters per breath. The sieve beds can be pressurized from atmosphere to ten pounds per square inch in 7 seconds. If the sieve beds can be pressurized from vacuum to ten pounds per square inch in seven seconds, using a pressure equalization cycle, then the concentrator may produce more oxygen than necessary for a patient's use. The concentrator may be turned off or two thirds of a minute for every minute. The quicker the molecular sieve beds pressurize, the higher the oxygen flows, and the longer the battery can operate between battery re-charging. During the pressurization cycle, the patient may breathe one breath of atmospheric air. This is in order to conserve oxygen. Sizing the molecular sieve beds correctly, so that they are not too large, will also affect this process as it should not take too long to pressurize the beds or else the patient may be breathing too much ambient air.

It has been found that replacing the four small port 24, 26, 42 and 46 valves, that in other embodiments controlled the pressurization of the molecular sieve beds, with one high flow control valve 152 may reduce the bed pressurization time. Valves 154 and 156 are added to allow the sieve beds to vent to atmosphere to reduce the time required to pressurize or evacuate the beds. This alleviates some of the load on the compressor. Typically pressurizing a molecular sieve bed from vacuum to ten pounds per square inch takes two times as long as pressurizing from zero to ten pounds per square inch. The pressure equalization valves 154 and 156 save for example 50 percent of the compressor time and power requirements.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A gas concentrator for enriching a target component gas concentration in a gas comprising:

a gas compressor and vacuum pump, an air-tight first container containing a molecular sieve material for adsorbing a waste component gas from the gas, and a second air-tight container containing molecular sieve material for adsorbing the waste component gas, wherein said first container is in fluid communication with said compressor and said vacuum pump through a first gas conduit, and said second container is in fluid communication with said compressor and said vacuum pump through a second gas conduit, wherein a third gas conduit connects said first and second containers in fluid communication with each other, and a fourth gas conduit cooperates with said third gas conduit for delivery of the target component gas along said fourth gas conduit to an end use, at least one selectively actuable first valve mounted to said first and second gas conduits, selectively actuable second and third valves mounted to said third gas conduit, a flow controller mounted between said second and third valves regulating said cooperation between said third and fourth gas conduits, a gas flow controller controlling actuation of said valves mounted to said gas conduits, said valves cooperating to regulate gas flow through said conduits so as to sequentially, in repeating cycles:

(a) prevent the gas from flowing between said first and second container and allow compressed gas from said compressor into said first container during a first gas pressurization phase, whereby said first container is pressurized to a threshold pressure level to create a first enriched gas packet having an incrementally enriched target component gas concentration, while simultaneously actuating said vacuum pump to evacuate said second container to a threshold vacuum level during a first evacuation phase whereby said second container is evacuated to said threshold evacuation level to remove a first waste gas packet whereby a target waste gas is removed from said second container and expelled to atmosphere, (b) prevent the gas from flowing between either of said containers and said compressor or said vacuum pump and allow a regulated amount of said first enriched gas packet to flow from said first container into said fourth gas conduit for delivery of the target component gas for said end use, downstream along said fourth gas conduit, (c) prevent the gas from flowing between either of said containers and said compressor or said vacuum pump or between either of said containers and said end use, and allow said first enriched gas packet to flow between said first and second containers from said first container into said second container during a first enriched gas packet flow phase, whereby the first enriched gas packet flows from the pressurized first container to the evacuated second container, and, (d) prevent the gas from flowing between said containers and actuate said compressor to pressurize said second container to said threshold pressure level to create a second enriched gas packet and simultaneously actuating said vacuum pump to depressurize said first container during a second evacuation phase and thereby remove a second waste gas packet whereby waste gas is removed from said first container and expelled to atmosphere, (e) prevent the gas from flowing between either of said containers and said compressor or said vacuum pump and allow a regulated amount of said second enriched gas packet to flow from said second container into said fourth gas conduit for delivery of the target component gas for said end use, downstream along said fourth gas conduit, (f) prevent the gas from flowing between either of said containers and said compressor or said vacuum pump or between either of said containers and said end use, and allow said second enriched gas packet to flow between said first and second containers from said second container into said first container during a second enriched gas packet flow phase, whereby the second enriched gas packet flows from the pressurized second container to the evacuated first container.

2. The device of claim 1 wherein the target component gas is oxygen, the waste component gas is nitrogen and said molecular sieve material is zeolite.

3. The device of claim 1 wherein said compressor and said vacuum pump are a combined compressor/vacuum pump in a single unit.

4. The device of claim 1 wherein said fourth gas conduit branches off said third gas conduit.

5. The device of claim 4 wherein a tee-junction branches said fourth gas conduit off said third gas conduit.

6. The device of claim 1 wherein said gas flow controller is a programmable logic controller.

7. The device of claim 1 wherein said gas flow controller is a hard-wired electrical circuit.

8. The device of claim 1 further comprising passive first and second one-way valves mounted in parallel to said compressor and said vacuum pump respectively so as to be in fluid communication with said first and second gas conduits when said compressor and said vacuum pump are respectively in fluid communication with said first and second gas conduits so that in-flow of gas from external to said concentrator during said first or second pressurization phase is simultaneously assisted by said first one-way valve, and so that out-flow of gas from said concentrator during said first or second evacuation phase is simultaneously assisted by said second one-way valve.

9. The device of claim 1 wherein said flow controller is a demand valve mounted on said fourth gas conduit.

10. The device of claim 9 wherein said demand valve opens to supply said target component gas along said fourth gas conduit upon triggering by a low pressure applied to a pressure sensor of said demand valve.

11. The device of claim 10 wherein said fourth gas conduit has a free end adapted for having a suction applied to it by a human end user.

12. For use with a gas concentrator for enriching a target component gas concentration in a gas, wherein the gas concentrator comprises:

a gas compressor and vacuum pump, an air-tight first container containing a molecular sieve material for adsorbing a waste component gas from the gas, and a second air-tight container containing molecular sieve material for adsorbing the waste component gas, wherein said first container is in fluid communication with said compressor and said vacuum pump through a first gas conduit, and said second container is in fluid communication with said compressor and said vacuum pump through a second gas conduit, wherein a third gas conduit connects said first and second containers in fluid communication with each other, and a fourth gas conduit cooperates with said third gas conduit for delivery of the target component gas along said fourth gas conduit to an end use, at least one selectively actuable first valve mounted to said first and second gas conduits, selectively actuable second and third valves mounted to said third gas conduit, a flow controller mounted between said second and third valves regulating said cooperation between said third and fourth gas conduits, a gas flow controller controlling actuation of said valves mounted to said gas conduits, said valves cooperating to regulate gas flow through said conduits, a method of concentrating and supplying to an end use a target component gas concentration comprising the steps of, sequentially, in repeating cycles:

(a) preventing the gas from flowing between said first and second container and allowing compressed gas from said compressor into said first container during a first gas pressurization phase, whereby said first container is pressurized to a threshold pressure level to create a first enriched gas packet having an incrementally enriched target component gas concentration, while simultaneously actuating said vacuum pump to evacuate said second container to a threshold vacuum level during a first evacuation phase whereby said second container is evacuated to said threshold evacuation level to remove a first waste gas packet whereby a target waste gas is removed from said second container and expelled to atmosphere, (b) preventing the gas from flowing between either of said containers and said compressor or said vacuum pump and allowing a regulated amount of said first enriched gas packet to flow from said first container into said fourth gas conduit for delivery of the target component gas for said end use, downstream along said fourth gas conduit, (c) preventing the gas from flowing between either of said containers and said compressor or said vacuum pump or between either of said containers and said end use, and allowing said first enriched gas packet to flow between said first and second containers from said first container into said second container during a first enriched gas packet flow phase, whereby the first enriched gas packet flows from the pressurized first container to the evacuated second container, (d) preventing the gas from flowing between said containers and actuating said compressor to pressurize said second container to said threshold pressure level to create a second enriched gas packet and simultaneously actuating said vacuum pump to de-pressurize said first container during a second evacuation phase and thereby remove a second waste gas packet whereby waste gas is removed from said first container and expelled to atmosphere, (e) preventing the gas from flowing between either of said containers and said compressor or said vacuum pump and allow a regulated amount of said second enriched gas packet to flow from said second container into said fourth gas conduit for delivery of the target component gas for said end use, downstream along said fourth gas conduit, and, (f) preventing the gas from flowing between either of said containers and said compressor or said vacuum pump or between either of said containers and said end use, and allowing said second enriched gas packet to flow between said first and second containers from said second container into said first container during a second enriched gas packet flow phase, whereby the second enriched gas packet flows from the pressurized second container to the evacuated first container.

13. The method of claim 12 wherein the target component gas is oxygen, the waste component gas is nitrogen and said molecular sieve material is zeolite, further comprising the step of supplying ambient air to said compressor.

14. The method of claim 12 further comprising the step of providing said compressor and said vacuum pump as a combined compressor/vacuum pump in a single unit.

15. The method of claim 12 comprising the step of branching said fourth gas conduit off said third gas conduit.

16. The method of claim 15 further comprising the step of providing a tee-junction for said branching of said fourth gas conduit off said third gas conduit.

17. The method of claim 12 further comprising the step of programming said gas flow controller wherein said controller is a programmable logic controller.

18. The method of claim 12 further comprising the step of providing passive first and second one-way valves mounted in parallel to said compressor and said vacuum pump respectively so as to be in fluid communication with said first and second gas conduits when said compressor and said vacuum pump are respectively in fluid communication with said first and second gas conduits so that in-flow of gas from external to said concentrator during said first or second pressurization phase is simultaneously assisted by said first one-way valve, and so that out-flow of gas from said concentrator during said first or second evacuation phase is simultaneously assisted by said second one-way valve.

19. The method of claim 18 further comprising the steps of:

during said first and second evacuation phases, firstly allowing de-pressurization to equivalent to the ambient pressure external to said concentrator through said second one-way valve and then actuating said vacuum pump to continue de-pressurization, and, during said first and second pressurization phases, firstly allowing pressurization to equivalent to the ambient pressure external to said concentrator through said first one-way valve and then actuating said compressor to continue pressurization.

* * * * *